(12) United States Patent
Mirkin et al.

(10) Patent No.: US 12,378,280 B2
(45) Date of Patent: Aug. 5, 2025

(54) DEOXYNUCLEIC GUANIDINES (DNG)-MODIFIED OLIGONUCLEOTIDES AND METHODS OF SYNTHESIZING DEOXYNUCLEIC GUANIDINE STRANDS

(71) Applicant: NORTHWESTERN UNIVERSITY, Evanston, IL (US)

(72) Inventors: Chad A. Mirkin, Wilmette, IL (US); Kacper Skakuj, Durham, NC (US); Katherine E. Bujold, Magog (CA)

(73) Assignee: NORTHWESTERN UNIVERSITY, Evanston, IL (US)

( * ) Notice: Subject to any disclaimer, the term of this patent is extended or adjusted under 35 U.S.C. 154(b) by 499 days.

(21) Appl. No.: 16/906,619

(22) Filed: Jun. 19, 2020

(65) Prior Publication Data
US 2020/0399304 A1 Dec. 24, 2020

Related U.S. Application Data

(60) Provisional application No. 62/870,639, filed on Jul. 3, 2019, provisional application No. 62/864,682, filed on Jun. 21, 2019, provisional application No. 62/864,720, filed on Jun. 21, 2019.

(51) Int. Cl.
| | | |
|---|---|---|
| *C07H 21/02* | (2006.01) | |
| *A61K 9/51* | (2006.01) | |
| *A61K 31/7125* | (2006.01) | |
| *A61K 47/02* | (2006.01) | |
| *C07H 21/04* | (2006.01) | |
| *C12N 15/11* | (2006.01) | |
| *C12N 15/113* | (2010.01) | |
| *C12N 15/85* | (2006.01) | |

(52) U.S. Cl.
CPC ............ *C07H 21/04* (2013.01); *A61K 9/5115* (2013.01); *A61K 31/7125* (2013.01); *A61K 47/02* (2013.01); *C12N 15/11* (2013.01); *C12N 15/113* (2013.01); *C12N 15/85* (2013.01); *C12N 2310/11* (2013.01); *C12N 2310/14* (2013.01)

(58) Field of Classification Search
CPC .............................. C12N 15/113; C12N 15/11
See application file for complete search history.

(56) References Cited

U.S. PATENT DOCUMENTS

| 5,696,253 A | 12/1997 | Bruice et al. |
| 6,136,965 A | 10/2000 | Bruice et al. |

FOREIGN PATENT DOCUMENTS

| WO | WO-96/00575 A1 | 1/1996 |

OTHER PUBLICATIONS

Yang et al., "Gold nanoparticle based fluorescent oligonucleotide probes for imaging and therapy in living systems" Analyst vol. 144 pp. 1052-1072 DOI: 10.1039/c8an02070a (Year: 2019).*
Zheng et al. (PNAS, 2012, 109, 30, 11975-11980).*
Sprangers et al. (Small, 13, 10, 2017, 1602753, 1-7).*
Jain et al. (Chem. Rev. 2012, 112, 3, 1284-1309).*
Albright et al., Denaturing Polyacrylamide Gel Electrophoresis, Curr. Protocols in Human Genetics, 00(1):A.3F.1-A.3F.4 (Apr. 1994).
Ali et al., A greener synthetic protocol for the preparation of carbodiimide, Tetrahedron Lett., 51(7):1019-21 (Feb. 2010).
Challa et al., Deoxynucleic guanidine; synthesis and incorporation of purine nucleosides into positively charged DNG oligonucleotides, Bioorg. Med. Chem., 12(6):1475-81 (Mar. 2004).
Convers et al., Preparation and evaluation of a polymer-supported Mukaiyama reagent, Tetrahedron Lett., 45(17):3401-4 (Apr. 2004).
Duangkamol et al., Ultrasonic-assisted synthesis of carbodiimides from N,N'-disubstituted thioureas and ureas, Monatshefte fur Chemie, 147(11):1945-9 (2016).
Eleuteri et al., Synthesis of 3',5'-dithiothymidine and related compounds, J. Chem Soc., Perkin Trans.1, 1(18):2237-40 (1996).
Gafffney et al., Synthesis of c-di-GMP analogs with thiourea, urea, carbodiimide, and guanidinium linkages, Org. Lett., 16(1):158-61 (Jan. 2014).
Kong et al., A versatile thiouronium-based solid-phase synthesis of 1,3,5-triazines, Chemistry, 18(5):1476-86 (2012).
Lavandera et al., First regioselective enzymatic acylation of amino groups applied to pyrimidine 3',5'-diaminonucleoside derivatives. Improved synthesis of pyrimidine 3',5'-diamino-2',3',5'-trideoxynucleosides, J. Org. Chem., 66(11):4079-82 (Jun. 2001).
Meng et al., Oligonucleotide analogues with cationic backbone linkages, Beilstein J. Org. Chem., 14:1293-308 (Jun. 2018).
Ruda et al., Modified 5'-trityl nucleosides as inhibitors of Plasmodium falciparum dUTPase, ChemMedChem., 6(2):309-20 (Feb. 2011).
Shibanuma et al., A Convenient Method for the Preparation of Carbodiimides Using 2-Chloropyridinium Salt, Chem. Lett., 6(5):575-6 (1977).
Sinha et al., Analysis and Purification of Synthetic Nucleic Acids Using HPLC, Curr. Protoc. Nucleic Acid Chem., 61:10.5.1-10.5.39 (Jun. 2015).
Skakuj et al., Automated Synthesis and Purification of Guanidine-Backbone Oligonucleotides, Curr. Protoc. Nucleic Acid Chem., 81(1):e110 (2020).
Skakuj et al., Mercury-Free Automated Synthesis of Guanidinium Backbone Oligonucleotides, J. Am. Chem. Soc., 141(51):20171-6 (Dec. 2019).
Yella et al., Tandem regioselective synthesis of tetrazoles and related heterocycles using iodine, Org. Biomol. Chem., 9(9):3235-45 (May 2011).

(Continued)

*Primary Examiner* — Amy Rose Hudson
(74) *Attorney, Agent, or Firm* — MARSHALL, GERSTEIN & BORUN LLP

(57) ABSTRACT

Disclosed herein are spherical nucleic acids (SNAs) comprising oligonucleotides comprising one or more modified oligonucleotides, and methods of use thereof. Also disclosed are methods of synthesizing modified oligonucleotides for use in therapeutics, including deoxynucleic guanidine (DNG)-modified oligonucleotides.

15 Claims, 49 Drawing Sheets

(56) References Cited

OTHER PUBLICATIONS

Choi, et al., Mechanism for the endocytosis of spherical nucleic acid nanoparticle conjugates, PNAS, vol. 110, No. 19, pp. 7625-7630 (2013).

* cited by examiner

CMPI: 2-chloro-1-methyl-pyridinium iodide; HTIB: hydroxy tosyloxy iodobenzene

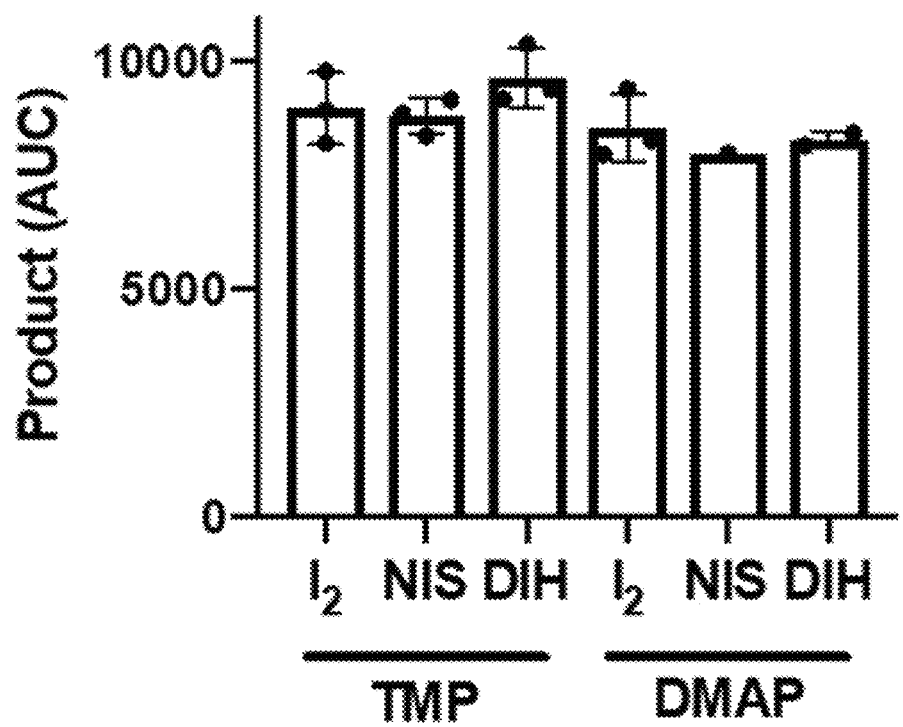
FIG. 3B
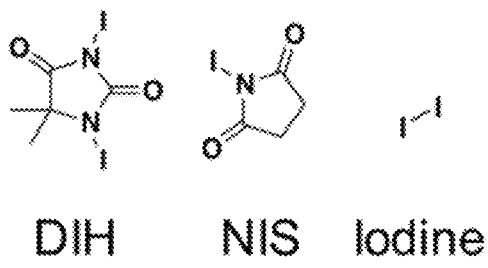
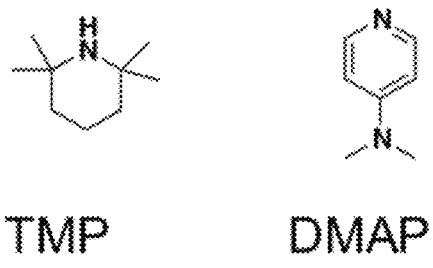
FIG. 3C

| Entry | Coupling Yield[a] | Thiourea / Iodine / Base | | Wash | Activator Age |
|---|---|---|---|---|---|
| | | Ratio | Concentration (mM) | | |
| 1 | 82% | 3/1/3 | 38/13/38 | ACN | <1h |
| 2 | 84% | 3/1/3 | 38/13/38 | ACN | 24h |
| 3 | 64% | 3/1/3 | 38/13/38 | ACN | 48h |
| 4[b] | 82% | 3/1/3 | 38/13/38 | DMF | <1h |
| 5 | 89% | 1.5/1/3 | 19/13/28 | DMF | <1h |
| 6 | 84% | 1/1/4 | 13/13/50 | DMF | <1h |
| 7 | 90% | 1/1/3 | 13/13/38 | DMF | <1h |
| 8 | 82% | 1/1/2 | 13/13/25 | DMF | <1h |

[a]Approximate yields based on AUC of HPLC A254 channel of solid phase synthesis on a MerMade12 synthesizer of (pT)$_{17}$(gT)$_3$. [b]Iodine extracted with saturated NaHCO$_3$ and dried with MgSO$_4$ prior to mixing the activator.

FIG. 5A

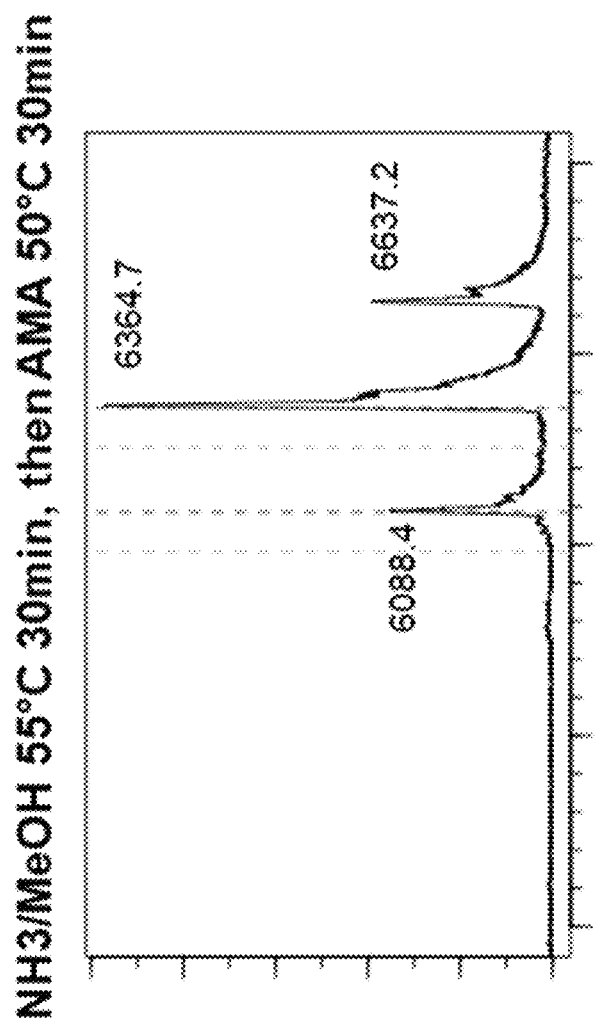

DNG-DNA Oligonucleotides – Characterization

| Name | Sequence (5'-3') | Expected mass | Experimental |
|---|---|---|---|
| T20 | HO-T-T-T-T-T-T$_{15}$-C$_3$-SH | 6262.9 | 6273.3 |
| 1+ 5' | HO-T+T-T-T-T-T$_{15}$-C$_3$-SH | 6229.3 | 6237.5 |
| 2+ 5' | HO-T+T+T-T-T-T$_{15}$-C$_3$-SH | 6192.4 | 6198.1 |
| 3+ 5' | HO-T+T+T+T-T-T$_{15}$-C$_3$-SH | 6155.5 | 6153.9 |
| 1+ 3' | HO-T$_{15}$-T-T-T-T+T-C$_3$-SH | 6229.3 | 6231.5 |
| 2+ 3' | HO-T$_{15}$-T-T-T+T+T-C$_3$-SH | 6192.4 | 6206.5 |
| 3+ 3' | HO-T$_{15}$-T-T+T+T+T-C$_3$-SH | 6155.5 | 6162.8 |

Masses acquired by MALDI-TOF with DHAP matrix

Oligonucleotides with deoxynucleic guanidine (DNG) inserts (blue) can be synthesized and characterized by MALDI reliably.

FIG. 12

Salt aging:
- DNA:AuNP at 1000:1 for 72h in $H_2O$
- No surfactant
- NaCl from 0 to 1M in 6h, then left for 16h
- Washed with 5x $H_2O$

3DNG/0DNG ratio = 0.49

Masses found by MALDI-MS

| Sample | Expected | Found |
|---|---|---|
| T14 – 6DNG | 6029.4 | 6030.1 |

FIG. 23B $R_1 = p(CH_2)_3SS(CH_2)_3OH$
$R_2 = MMTr$

A) T$_m$ for DNA-DNG duplexes with 0-3 DNG

B) Melting transition of DNA-DNG duplexes with 0-3 DNG

A) CD for single-stranded DNA-DNG strands with 0-3 DNG

B) CD for A20:T20 DNA-DNG duplexes with 0-3 DNG

C) CD for single-stranded DNA-DNG strands with 0, 3 or 6 DNG

GelRed

Stainsall

Loading of salt aged SNAs

Loading of freeze-thawed SNAs

SNAs with DNG linkages

C) Relative uptake after NaN₃-DOG treatment

D) Relative uptake after chlorpromazine treatment

DEOXYNUCLEIC GUANIDINES (DNG)-MODIFIED OLIGONUCLEOTIDES AND METHODS OF SYNTHESIZING DEOXYNUCLEIC GUANIDINE STRANDS

STATEMENT OF GOVERNMENT INTEREST

This invention was made with government support under U54 CA199091 awarded by the National Institutes of Health (NIH) and N00014-15-1-0043 awarded by the Office of Naval Research (ONR). The government has certain rights in the invention.

FIELD

The present disclosure is directed to the synthesis and use of spherical nucleic acids (SNAs) comprising modified oligonucleotides in therapeutics. The disclosure provides methods of synthesizing and using such modified oligonucleotides, including deoxynucleic guanidines (DNG)-modified oligonucleotides and oligonucleotides comprising positively-charged deoxynucleic guanidine (DNG) inserts.

BACKGROUND

Spherical nucleic acids (SNAs) comprise densely functionalized and highly oriented polynucleotides on the surface of a nanoparticle, which can either be inorganic (such as gold, silver, or platinum) or organic (such as liposomal). The spherical architecture of the polynucleotide shell confers unique advantages over traditional nucleic acid delivery methods, including entry into nearly all cells independent of transfection agents and resistance to nuclease degradation. The rapid and extensive cellular uptake of spherical nucleic acids (SNAs)—highly oriented oligonucleotides densely functionalized onto nanoparticle cores—is dictated by their preferential interaction with scavenger receptors of class A. This specific interaction, which has directed their path as therapeutics, is guided by the DNA shell of SNAs, mainly through its highly packed structure and densely charged backbone. Unfortunately, this pathway typically leads to cellular uptake through endocytosis and further escape from these vesicles is impeded by the dense negative charge and hydrophilicity of SNAs.

Recent progress in the synthesis of deoxynucleic guanidine (DNG)—oligonucleotides with a permanent cationic backbone—has provided the ability to overcome these shortcomings and to study the impact of programmed surface charge modifications on SNA uptake.

Modification of oligonucleotides that are not found in nature have been crucial to their translation into the clinic—all clinically viable oligonucleotide-based therapeutics contain unnatural modifications. One example of oligonucleotide modification is the replacement of negatively-charged phosphate backbones with positively-charged guanidinium linkages. Previous publications have shown that these types of strands hybridize with complementary oligonucleotide sequences and resist nuclease degradation, both crucial components for therapeutic applications. Furthermore, guanidinium backbone modifications could have significant implications on the interactions of these structures with cells, such as rapid cellular uptake and endosomal escape, based on published findings using structures that contain multiple positive charges or guanidinium moieties (polymers, nanoparticles, proteins, etc.).

SUMMARY

The present disclosure demonstrates that increasing the number of DNG inserts near the surface of SNAs significantly increases the extent of cellular uptake. This effect is likely mediated by interactions of guanidines at the cellular membrane level with charged head groups of fatty acids and lipids, which leads to further internalization. These findings open the door to the rational design of SNAs with controlled uptake mechanisms, thus expanding their therapeutic scope, and hold promise for cationic oligonucleotide drug design.

In order to take advantage of the many beneficial qualities for therapeutic purposes, large amounts of guanidinium-backbone oligonucleotides need to be synthesized. The synthetic method disclosed herein removes the need for toxic reagents during such synthesis and the method can be completed on an automated synthesizer, an industry standard.

Oligonucleotides bearing guanidinium linkages have been synthesized previously using methods that employ stoichiometric amounts of mercury and excess thiophenol, both toxic reagents. The toxicity of these reagents and their potential to persistently contaminate laboratory equipment (such as expensive automated laboratory synthesizers) restrict the use of these previous methods to small-scale synthesis in an organic chemistry lab. Accordingly, there is a need for an improved method for synthesizing oligonucleotides modified with DNG inserts that can be scaled and applied to automated peptide synthesis.

In one aspect, the disclosure provides spherical nucleic acids (SNAs) comprising a nanoparticle functionalized with an oligonucleotide comprising at least one deoxynucleic guanidine residue (DNG).

In another aspect, the disclosure provides methods for synthesizing a deoxynucleic guanidine oligonucleotide comprising admixing an aminonucleoside with a thiourea nucleoside in the presence of an electrophilic iodine reagent, a base, and a solvent to form a deoxynucleic guanidine oligonucleotide, wherein the base has a $pK_a$ of about 7 to about 11, lacks α-protons, or both. In some embodiments, the electrophilic iodine reagent can be iodine ($I_2$). In some embodiments, the base can be 2,2,6,6-tetramethylpiperidine (TMP).

Further provided are methods of transfecting a cell comprising contacting the cell with an SNA disclosed herein. Further provided are methods for treating a disease or disorder comprising administering a therapeutically effective amount of the SNA.

BRIEF DESCRIPTION OF THE DRAWINGS

FIG. 3B shows a comparison of relative quantities of product produced with different combinations of coupling reagents and bases, and FIG. 3C shows structures of various coupling reagents and bases used herein (DIH: 1,3-diiodo-5,5-dimethylhydantoin; TMP: 2,2,6,6-tetramethylpiperidine; NIS: N-iodosuccinimide; DMAP: 4-dimethylaminopyridine).

FIG. 4A shows structures of various bases used herein, and FIG. 4B relative amounts of product formed using various bases described herein.

FIGS. 5A and 5B show the effect of reagent equivalents on reaction yield. FIG. 5A shows the optimization of the reaction on a solid support. Activator is stable up to 24 hours (entries 1-3), excess thiourea decreases yield (entries 4, 5, and 7), and 3 equiv. of base results in the highest yields (entries 6-8). FIG. 5B shows the optimization of the reaction in solution.

FIG. 6A shows the structure of synthesized DNA-DNG mixed strand. FIG. 6B shows the MALDI-TOF MS spectrum of a synthesized DNA-DNG mixed strand.

FIG. 7A shows a primarily DNG-containing strand as described herein, FIG. 7B shows the MALDI-TOF MS spectrum of a primarily DNG-containing strand as described herein, and FIG. 7C shows the SDS-PAGE characterization of a primarily DNG-containing strand as described herein.

FIGS. 9A-9D show that alkaline treatment at elevated temperature fails to cleave benzoyl groups from DNG-oligonucleotides described herein. FIG. 9A shows MALDI-TOF MS spectra of DNG-oligonucleotides protected with benzoyl groups following cleavage from solid support via treatment with AMA (40% aqueous ammonia and 40% aqueous methylamine) at 55° C. for 30 minutes. FIG. 9B shows MALDI-TOF MS spectra of DNG-oligonucleotides protected with benzoyl groups following cleavage from solid support via treatment with AMA at 80° C. for 30 minutes. FIG. 9C shows MALDI-TOF MS spectra of DNG-oligonucleotides protected with benzoyl groups following cleavage from solid support via treatment with ammonia in methanol at 55° C. for 30 minutes, followed by AMA at 50° C. for 30 minutes. FIG. 9D shows a benzoyl-protected DNG nucleoside as disclosed herein.

FIG. 12 is a chart showing a summary of MALDI-TOF characterization of DNG oligonucleotides as described herein.

FIGS. 16A and 16B are a chart and photograph showing that: FIG. 16A: loading of fluorescent labeled DNG-oligonucleotides onto SNAs decreases with increasing number of positively-charged DNG linkages, and FIG. 16B: increasing salt concentration leads to "sticking" of SNAs on tubes.

FIG. 17A shows this as measured by strands per nanoparticle, and FIG. 17B shows this as measured by DNA per nanoparticle.

FIGS. 23A-23E show that longer DNG inserts near the surface of SNAs further increase uptake. FIG. 23A: HPLC trace of a DNG oligonucleotide as synthesized herein; FIG. 23B: expected versus found masses of DNG oligonucleotide as synthesized herein as measured by MALDI-MS; FIG. 23C: gel showing retention of SNAs functionalized with 20-mer oligonucleotides comprising, from left to right, 0, 3, and 6 DNG inserts; FIG. 23D: uptake by C166-GFP cells of gold SNAs comprising 0, 3, or 6 DNG inserts; FIG. 23E: confocal microscopy image of C166-GFP cells treated with gold SNAs comprising 0, 3, or 6 DNG inserts.

FIG. 27A shows the structure of DNA-DNG chimeras as disclosed herein; FIG. 27B shows HPLC traces of chimeras with 3 DNG bases; FIG. 27C shows HPLC traces of chimeras with 6 DNG bases;

FIG. 27D shows HPLC traces of chimeras with 9 DNG bases. In each of FIGS. 27B-27D, the labeled peaks are failure (A), success (B), and assembly (C).

FIG. 28A shows a $T_m$ determination for DNA-DNG duplexes with 0-3 DNG inserts. FIG. 28B shows a melting transition determination for DNA-DNG duplexes with 0-3 DNG inserts. FIG. 28C shows a $T_m$ determination for DNA-DNG duplexes with 0, 3, or 6 DNG inserts. FIG. 28D shows a melting transition determination for DNA-DNG duplexes with 0, 3, or 6 DNG inserts.

FIG. 29A shows a CD trace for single-stranded DNA-DNG strands with 0-3 DNG inserts. FIG. 29B shows a CD trace for A20 DNA-DNG duplexes with 0-3 DNG inserts. FIG. 29C shows a CD trace for single-stranded DNA-DNG strands with 0, 3, or 6 DNG inserts.

FIG. 30A shows gel electrophoresis of DNA-DNG chimeras with 0, 3, or 6 DNG inserts and stained with GelRed®. FIG. 30A shows gel electrophoresis of DNA-DNG chimeras with 0, 3, or 6 DNG inserts and stained with Stains-all.

FIG. 31A shows loading of salt-aged SNAs with 0, 3, or 6 DNG inserts. FIG. 31B shows loading of freeze-thawed SNAs with 0, 3, or 6 DNG inserts. FIG. 31C shows a gel electrophoresis experiment comparing the traces of DNG SNAs prepared via salt-aging or freeze-thaw.

FIG. 32A shows the zeta potential of SNAs comprising oligonucleotides with 0-3 DNG modifications. FIG. 32B shows the zeta potential of SNAs comprising oligonucleotides with 0, 3, or 6 DNG modifications.

FIG. 34A shows the relative uptake of DNG SNAs after fucoidan treatment. FIG. 34B shows the relative uptake of DNG SNAs after sodium azide and 2-deoxyglucose ($NaN_3$-DOG) treatment. FIG. 34C shows the relative uptake of DNG SNAs after chlorpromazine treatment. FIG. 34D shows the results of a receptor blocking study for SNAs with 0, 3, or 6 DNG inserts.

DETAILED DESCRIPTION

The cationic and mixed charge oligonucleotides as described herein can be densely functionalized onto nanoparticle cores to produce spherical nucleic acids with controlled-charge DNA shells.

In some aspects, the disclosure provides a spherical nucleic acid (SNA) that comprises a modified oligonucleotide of the disclosure, e.g., a deoxynucleic guanidine oligonucleotide (DNG oligonucleotide). Spherical nucleic acids (SNAs) comprise densely functionalized and highly oriented polynucleotides on the surface of a nanoparticle which can either be inorganic (such as gold, silver, or platinum), organic (such as liposomal). The spherical architecture of the polynucleotide shell confers unique advantages over traditional nucleic acid delivery methods, including entry into nearly all cells independent of transfection agents and resistance to nuclease degradation.

Figure 15:
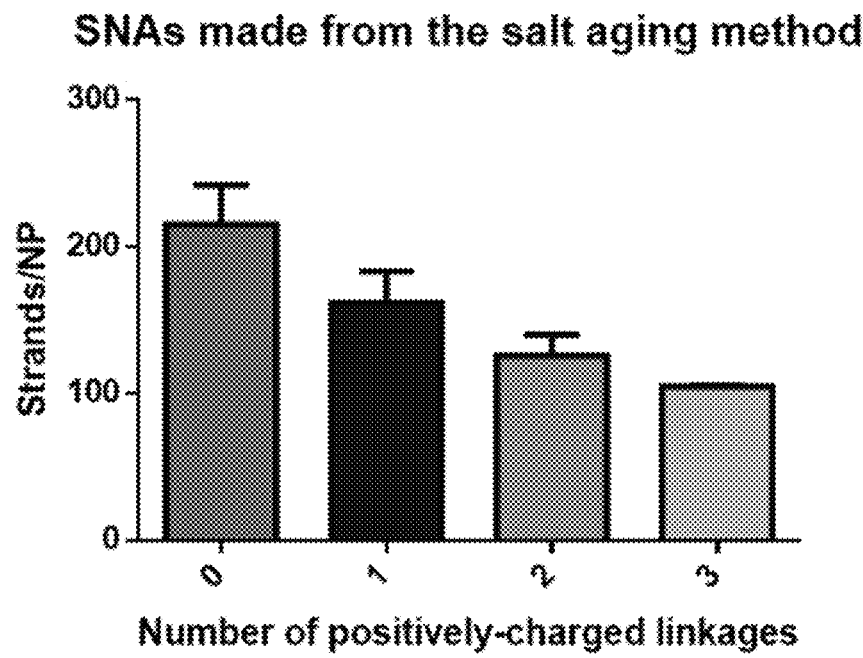
FIG. 15 is a chart showing the impact of an increasing number of inserts on the functionalization of DNG-modified SNAs.
Figure 16A:
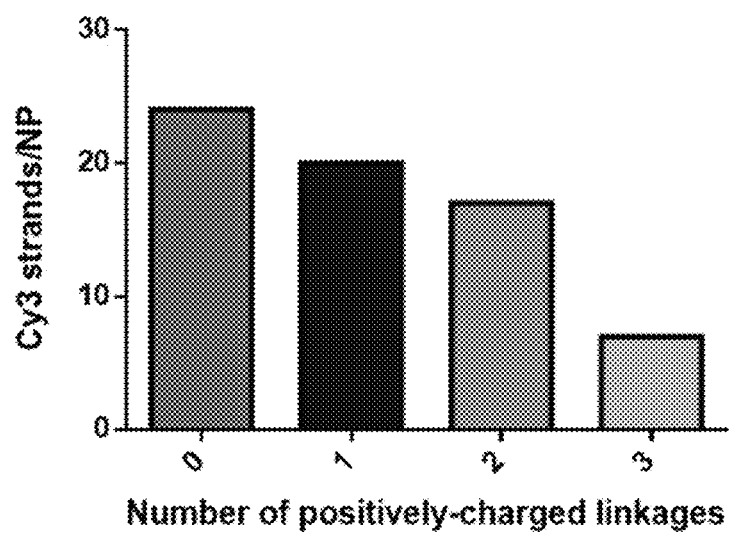
Figure 16B:
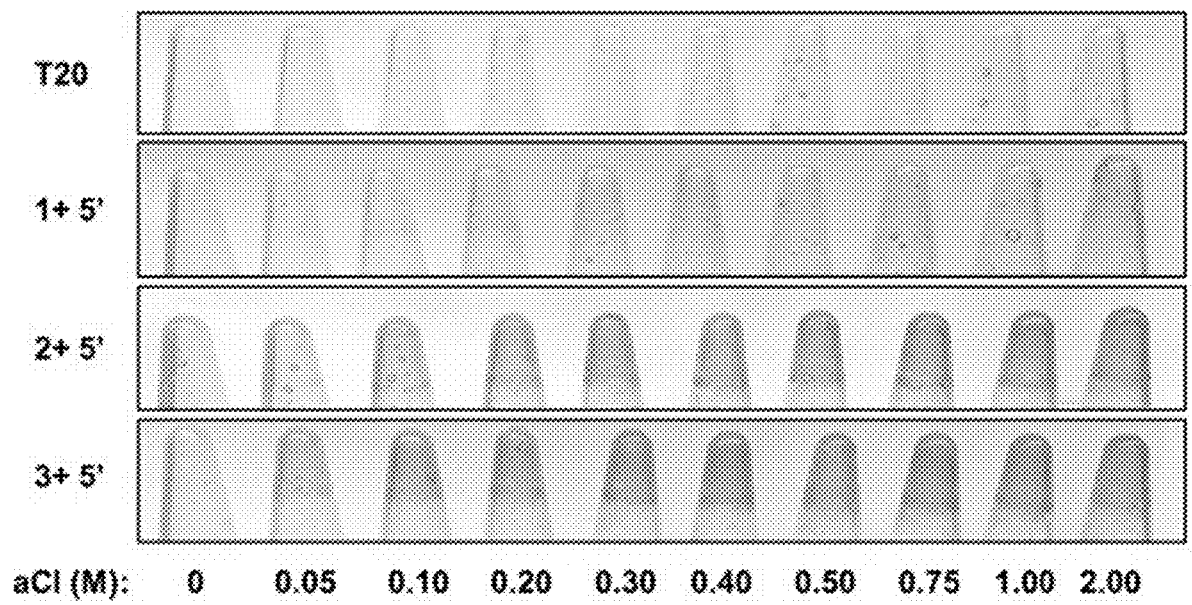
Figures 17A, 17B:
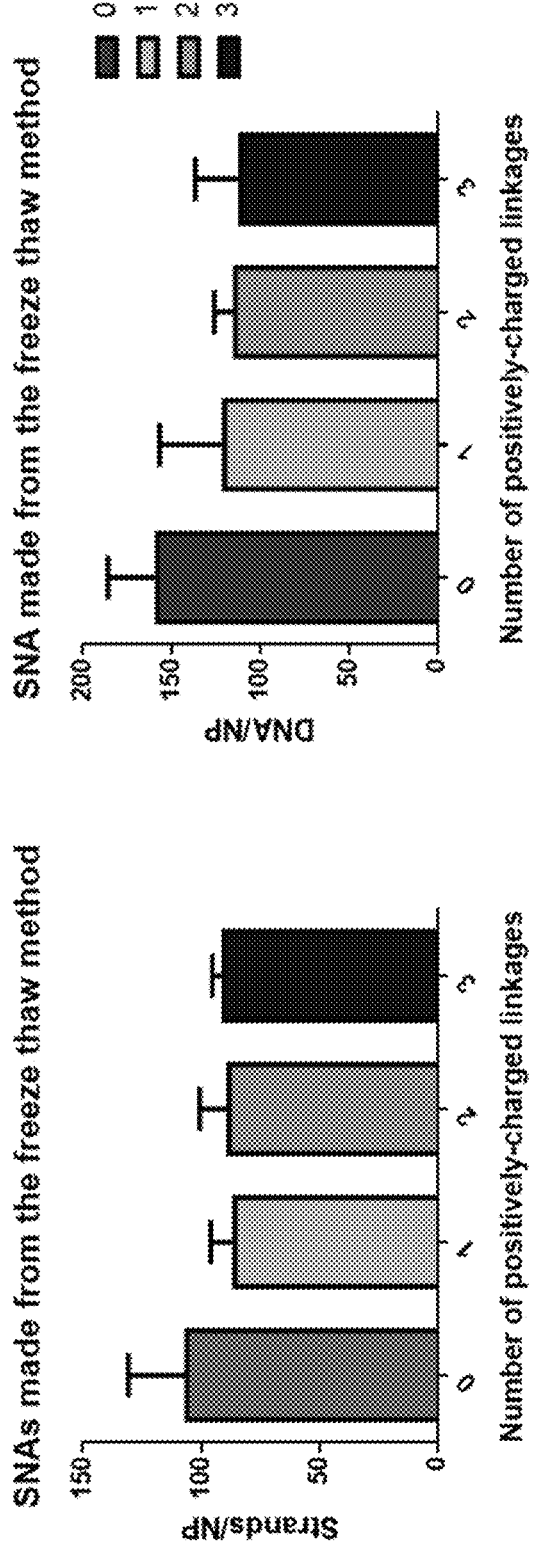
FIGS. 17A and 17B show that the freeze-thaw method gives more consistent DNG-DNA loadings onto gold nanoparticles.
Figure 18A:
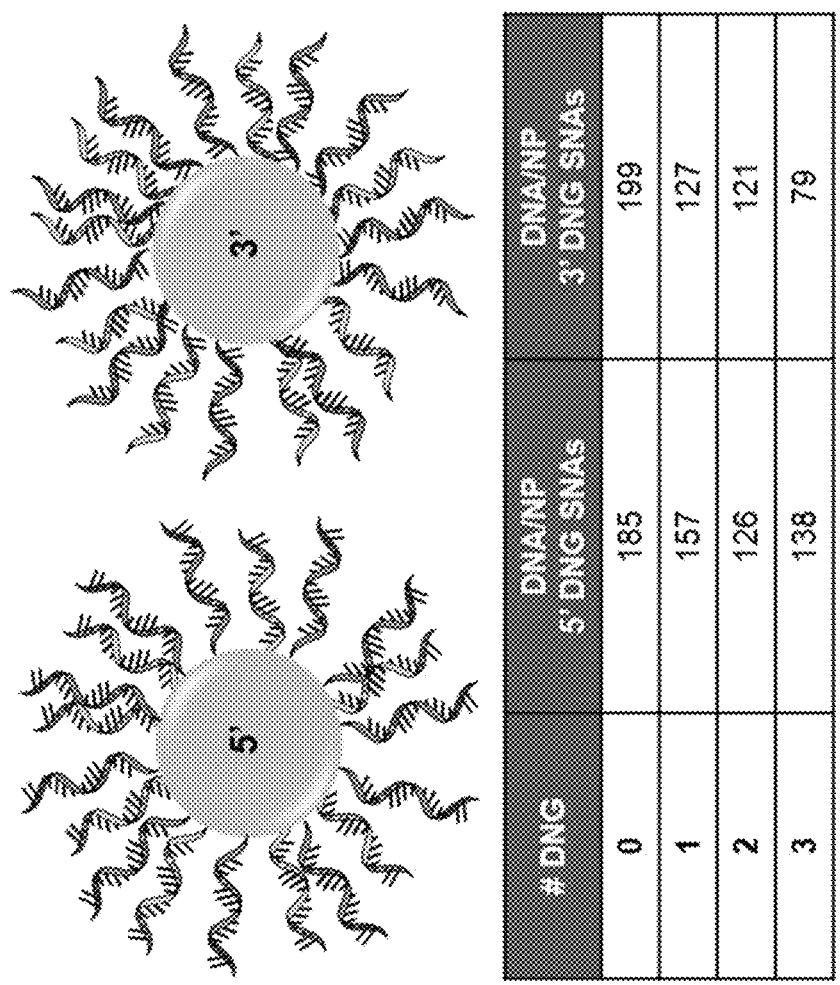
FIG. 18A shows that increasing numbers of DNG inserts at either the 3' or 5' end of the oligonucleotide decreases the loading when the 3' end is attached to the gold nanoparticle.
Figure 18B:
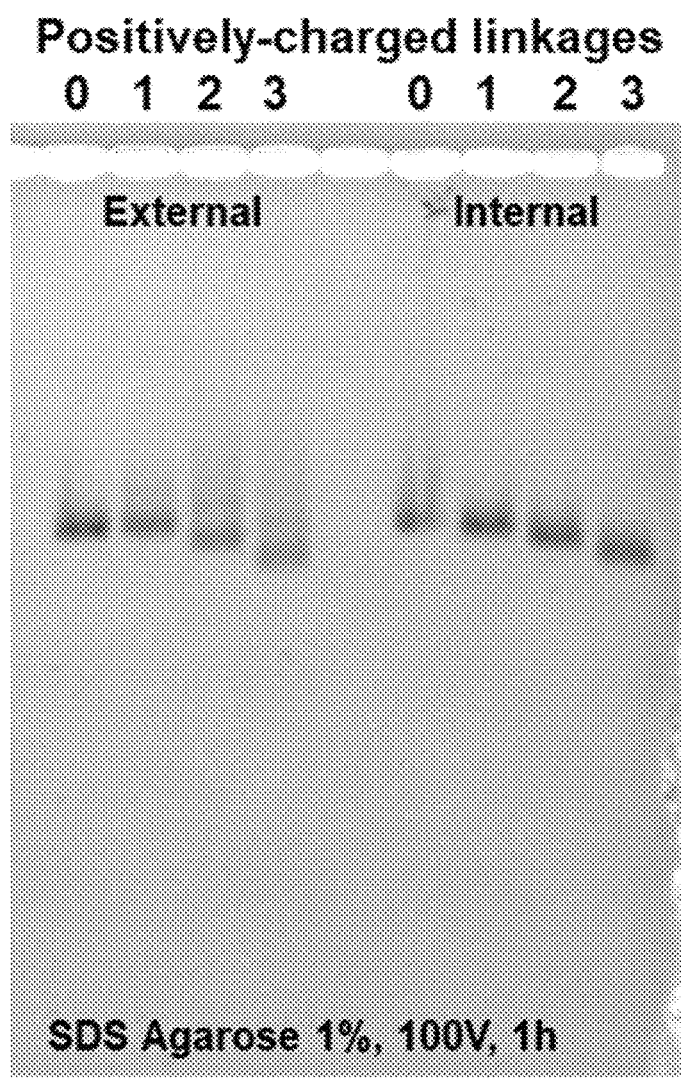
FIG. 18B is a gel showing the increased aggregation and self-assembly of SNAs when the DNG inserts are present on the 5' end of the oligonucleotide.

In some aspects, the disclosure provides SNAs comprising a nanoparticle functionalized with an oligonucleotide comprising at least one deoxynucleic guanidine modification (DNG modification). DNG-modified SNAs can be reliably synthesized using the salt aging method (see e.g., Hurst et al., *Anal. Chem.* 2006, 78 (24), 8313-8318); however, the number of DNG inserts negatively impacts SNA functionalization (FIGS. 15 and 16). It was observed that increasing salt concentrations in the absence of surfactants led to "sticking" of the nanoparticles onto tubes (FIG. 16B). DNG-modified SNAs can also be synthesized via the freeze-thaw method. In some cases, DNG-modified SNAs have a more consistent DNG-DNA loading than SNAs made e.g., via the salt aging method (FIG. 17). The location of the DNG insert on the DNA dictates assembly behavior-3' DNG-modified SNAs do not adopt secondary structures, contrary to their 5'-modified counterparts, which can sustain protein denaturation conditions (FIG. 18).

In some cases, the nanoparticle can include an inorganic material. For example, the nanoparticle can include gold, silver, or platinum. In some cases, the nanoparticle is or includes gold. In some cases, the nanoparticle can include an organic material. For example, the nanoparticle can be a liposome. In embodiments the nanoparticle is a micelle. In some embodiments, the nanoparticle is polymeric. In further embodiments, the nanoparticle comprises poly (lactic-co-glycolic acid) (PLGA). In some embodiments, the nanoparticle is metallic. In further embodiments, the nanoparticle is a colloidal metal. In still further embodiments, the nanoparticle is selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel nanoparticle.

In various embodiments, a nanoparticle of the disclosure is less than or equal to about 50 nanometers. In some embodiments, a plurality of SNAs is produced and the nanoparticles in the plurality of SNAs have a mean diameter of less than or equal to about 50 nanometers (e.g., about 5 nanometers to about 50 nanometers, or about 5 nanometers to about 40 nanometers, or about 5 nanometers to about 30 nanometers, or about 5 nanometers to about 20 nanometers, or about 10 nanometers to about 50 nanometers, or about 10 nanometers to about 40 nanometers, or about 10 nanometers to about 30 nanometers, or about 10 nanometers to about 20 nanometers). In further embodiments, the nanoparticles in the plurality of SNAs have a mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers. In some embodiments, the nanoparticle is a liposome.

In some embodiments, the oligonucleotide is bound to said nanoparticle through one or more sulfur linkages. In further embodiments, the oligonucleotide is from about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length. In some cases, the oligonucleotide comprises 1 to 20 nucleotides. In some cases, the oligonucleotide comprises 10 nucleotides. In still further embodiments, the oligonucleotide comprises RNA or DNA. In some embodiments, the RNA is selected from the group consisting of a small inhibitory RNA (siRNA), a single-stranded RNA (ssRNA) that forms a triplex with double stranded DNA, and a ribozyme. In some embodiments, the RNA is a microRNA. In further embodiments, the DNA is antisense-DNA or a catalytically active DNA molecule (DNAzyme).

In some cases, the oligonucleotide comprises 1 to 20 DNG units (DNGs). In some cases, the oligonucleotide comprises 1 to 10 DNGs. In some cases, the oligonucleotide comprises 1 to 8 DNGs. In some cases, the oligonucleotide comprises 1 to 6 DNGs. In some cases, the oligonucleotide comprises 1 to 3 DNGs. In some cases, the oligonucleotide comprises 6 DNGs. In some cases, the oligonucleotide comprises 3 DNGs. In some cases, the oligonucleotide comprises 2 DNGs. In some cases, the oligonucleotide comprises 1 DNG.

In some cases, least one DNG comprises adenine, guanine, thymine, uracil, or cytosine. In some cases, least one DNG comprises thymine, uracil, or cytosine. In some cases, least one DNG comprises thymine.

In some cases, the oligonucleotide comprises at least one DNG at the 5' end. In some cases, the oligonucleotide comprises one DNG at the 5' end. In some cases, the oligonucleotide comprises two DNGs at the 5' end. In some cases, the oligonucleotide comprises three DNGs at the 5' end. In some cases, the oligonucleotide comprises at least one DNG at the 3' end. In some cases, the oligonucleotide comprises one DNG at the 3' end. In some cases, the oligonucleotide comprises two DNGs at the 3' end. In some cases, the oligonucleotide comprises three DNGs at the 3' end. In some cases, the oligonucleotide comprises at least one DNG at the both the 5' and 3' ends.

Nanoparticle Surface Density.

A surface density adequate to make the nanoparticles stable and the conditions necessary to obtain it for a desired combination of nanoparticles and polynucleotides can be determined empirically. Generally, a surface density of at least about 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm2, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Alternatively, the density of polynucleotide on the surface of the SNA can be measured by the number of oligonucleotides on the surface of a SNA. With respect to the surface density of oligonucleotides on the surface of a SNA of the disclosure, it is contemplated that a SNA as described herein can have from about 1 to about 500 oligonucleotides on its surface. In further embodiments, a SNA can have from about 150 to about 350 oligonucleotides on its surface. In further embodiments, a SNA can have from about 200 to about 300 oligonucleotides on its surface. In various embodiments, a SNA can have from about 10 to about 100, or from 10 to about 90, or from about 10 to about 80, or from about 10 to about 70, or from about 10 to about 60, or from about 10 to about 50, or from about 10 to about 40, or from about 10 to about 30, or from about 10 to about 20 oligonucleotides on its surface. In further embodiments, a SNA can have about, at least about, or less than about 5, 10, 20, 30, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 oligonucleotides on its surface.

Methods of Treatment

Applications of the methods of the disclosure include, but are not limited to, antisense (AS) oligonucleotide therapeutics, siRNA delivery, and/or spherical nucleic acid (SNA)-based therapeutics. A SNA of the disclosure is contemplated, in various aspects and embodiments, to further include a therapeutic. The therapeutic may be encapsulated in the SNA, conjugated to the surface of the SNA, administered concurrently with the SNA, or a combination thereof.

In various embodiments, the therapeutic is a small molecule, an additional oligonucleotide, a protein, or a peptide.

Cationic DNG inserts increase cellular uptake of SNAs (see FIGS. 19-22). The length of the DNG insert can also have an effect on cellular uptake of SNAs. For example, SNAs with 6 DNG inserts near the surface show increased cellular uptake by confocal microscopy and ICP-MS (FIG. 23). The altered uptake mechanism can change the biodistribution of SNAs inside the body (e.g., change distribution into cells, tissues, and organs) or alter the pharmacokinetics of SNAs (e.g., alter the blood circulation half-life). In some cases, these changes can increase the amount of SNA in diseased tissues or decrease the amount of SNAs in tissues that cause unwanted side effects. In some cases, the altered uptake mechanism can affect the trafficking of SNAs inside cells (e.g., allow SNAs to be localized to different parts of cells). In some cases, the altered uptake mechanism can improve therapeutic efficacy with respect to other cellular delivery systems known in the art.

Provided herein are methods for transfecting a cell comprising contacting the cell with an SNA as disclosed herein. In some cases, contacting the cell occurs in vitro or in vivo. In some cases, contacting the cell occurs in vitro. In some cases, contacting the cell occurs in vivo.

Also provided are methods for treating diseases and disorders comprising administering a therapeutically effective amount of an SNA as disclosed herein. Non-limiting examples of diseases and disorders which can be treated via administration of an SNA as disclosed herein include cancer, nephropathy, diabetes type I, diabetes type II, renal disease glomerulonephritis, bacterial or viral glomerulonephritides, IgA nephropathy, Henoch-Schonlein Purpura, membranoproliferative glomerulonephritis, membranous nephropathy, Sjogren's syndrome, nephrotic syndrome minimal change disease, focal glomerulosclerosis and related disorders, acute renal failure, acute tubulointerstitial nephritis, pyelonephritis, GU tract inflammatory disease, pre-eclampsia, renal graft rejection, leprosy, reflux nephropathy, nephrolithiasis, genetic renal disease, medullary cystic, medullar sponge, polycystic kidney disease, autosomal dominant polycystic kidney disease, autosomal recessive polycystic kidney disease, tuberous sclerosis, von Hippel-Lindau disease, familial thin-glomerular basement membrane disease, collagen III glomerulopathy, fibronectin glomerulopathy, Alport's syndrome, Fabry's disease, Nail-Patella Syndrome, congenital urologic anomalies, monoclonal gammopathies, multiple myeloma, amyloidosis and related disorders, febrile illness, familial Mediterranean fever, HIV infection, AIDS, inflammatory disease, systemic vasculitides, polyarteritis nodosa, Wegener's granulomatosis, polyarteritis, necrotizing and crecentic glomerulonephritis, polymyositis-dermatomyositis, pancreatitis, rheumatoid arthritis, systemic lupus erythematosus, gout, blood disorders, sickle cell disease, thrombotic thrombocytopenia purpura, Fanconi's syndrome, transplantation, acute kidney injury, irritable bowel syndrome, hemolytic-uremic syndrome, acute cortical necrosis, renal thromboembolism, trauma and surgery, extensive injury, burns, abdominal and vascular surgery, induction of anesthesia, side effect of use of drugs or drug abuse, circulatory disease myocardial infarction, cardiac failure, peripheral vascular disease, hypertension, coronary heart disease, non-atherosclerotic cardiovascular disease, atherosclerotic cardiovascular disease, skin disease, psoriasis, systemic sclerosis, respiratory disease, COPD, obstructive sleep apnea, hypoia at high altitude or endocrine disease, acromegaly, diabetes mellitus, and diabetes insipidus.

Synthesis of Deoxynucleic Guanidine (DNG) Oligonucleotides

Published DNG syntheses have major drawbacks, including the use of toxic mercury and thiophenol-mercury complexes, which are unpleasant to use and contaminate laboratory instruments. These drawbacks preclude using the published methods for DNG oligonucleotide synthesis on automated oligonucleotide synthesizers, and relegate the synthesis of DNG oligonucleotides to organic synthesis laboratories, preventing further development and biological characterization.

Figure 1:
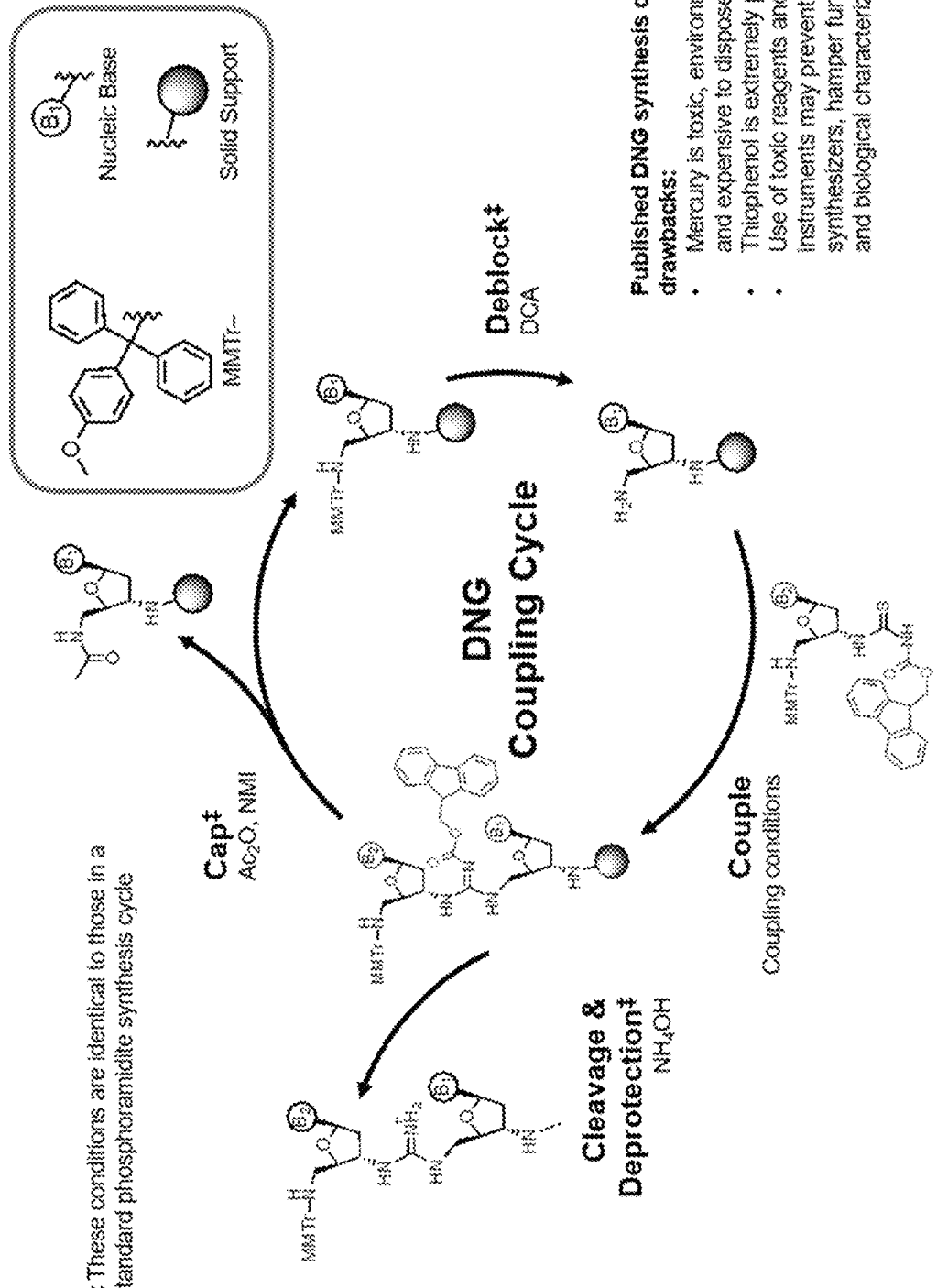
FIG. 1 shows a schematic of the coupling cycle used to prepare DNGs described herein.
Figure 2A:
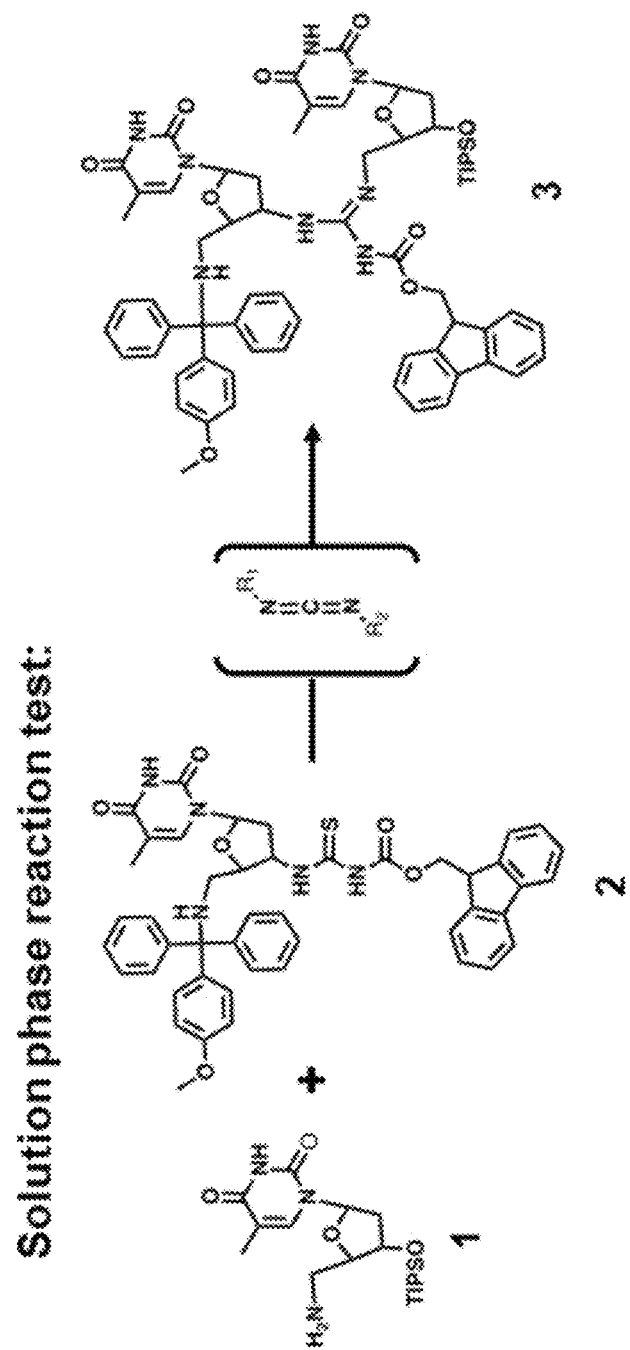
FIG. 2A shows a schematic of a solution-phase iodine-mediated nucleoside coupling.
Figure 2B:
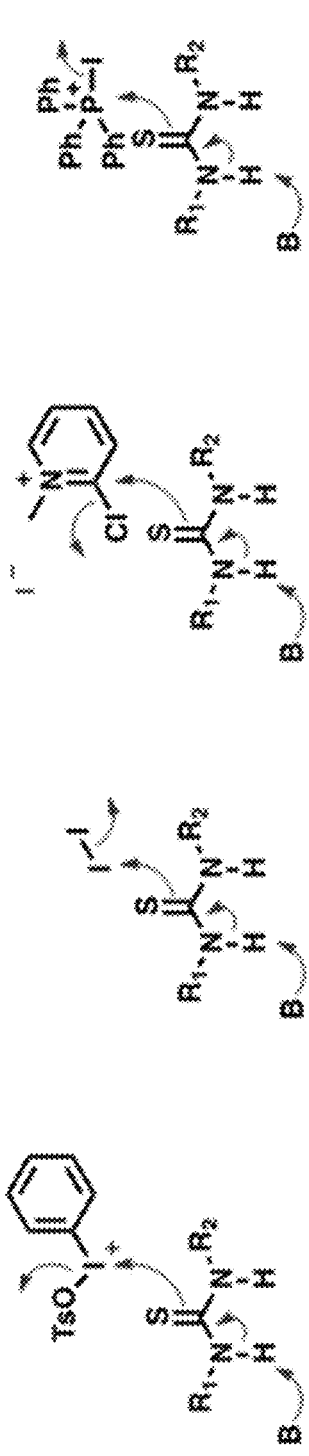
FIG. 2B shows putative mechanisms for iodine-mediated nucleoside coupling reactions, and FIG. 2C UPLC-MS analysis of iodine-mediated nucleoside coupling reactions, showing the relative amounts of starting materials ("SM") or product after one minute.
Figure 2C:
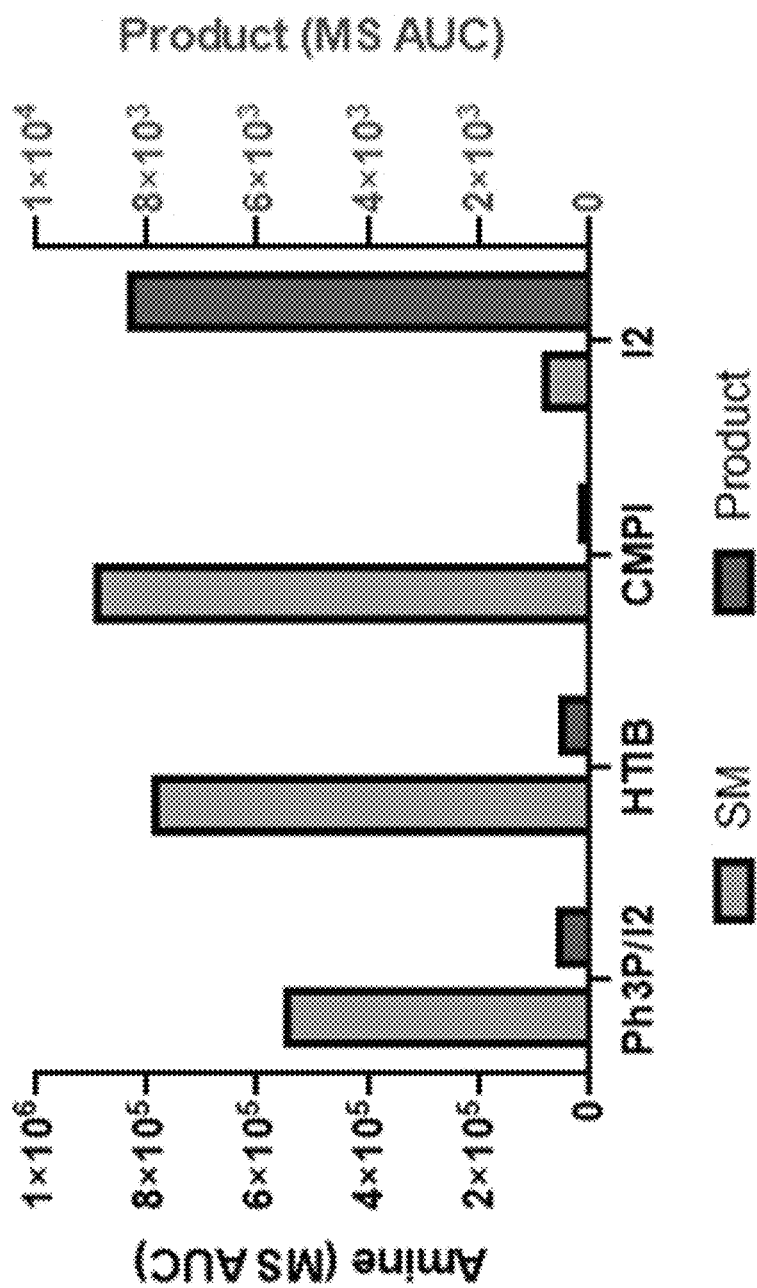
Figure 4A:
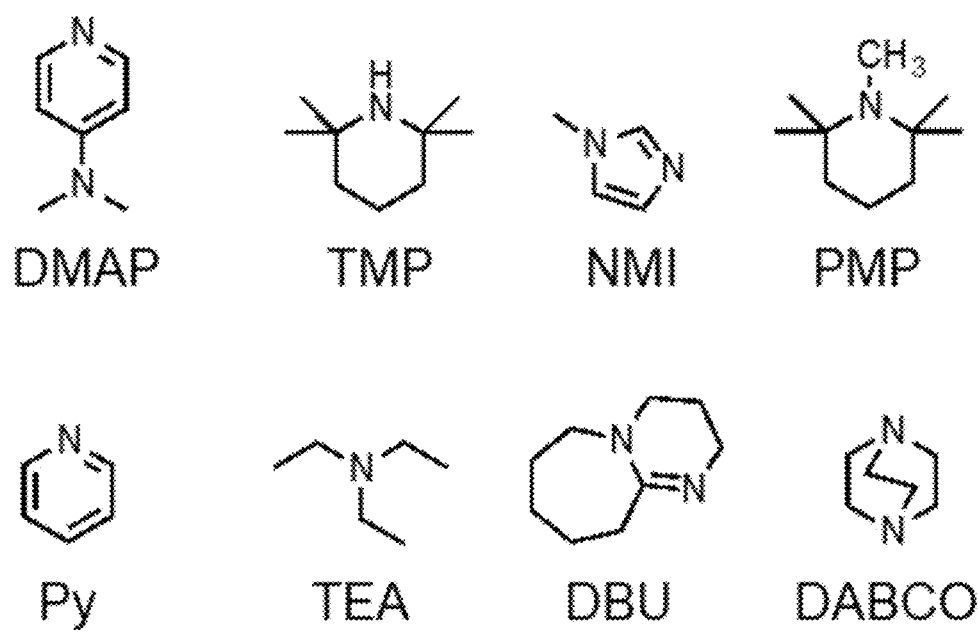
FIGS. 4A and 4B show the effect of base identity on reaction yield.
Figure 4B:
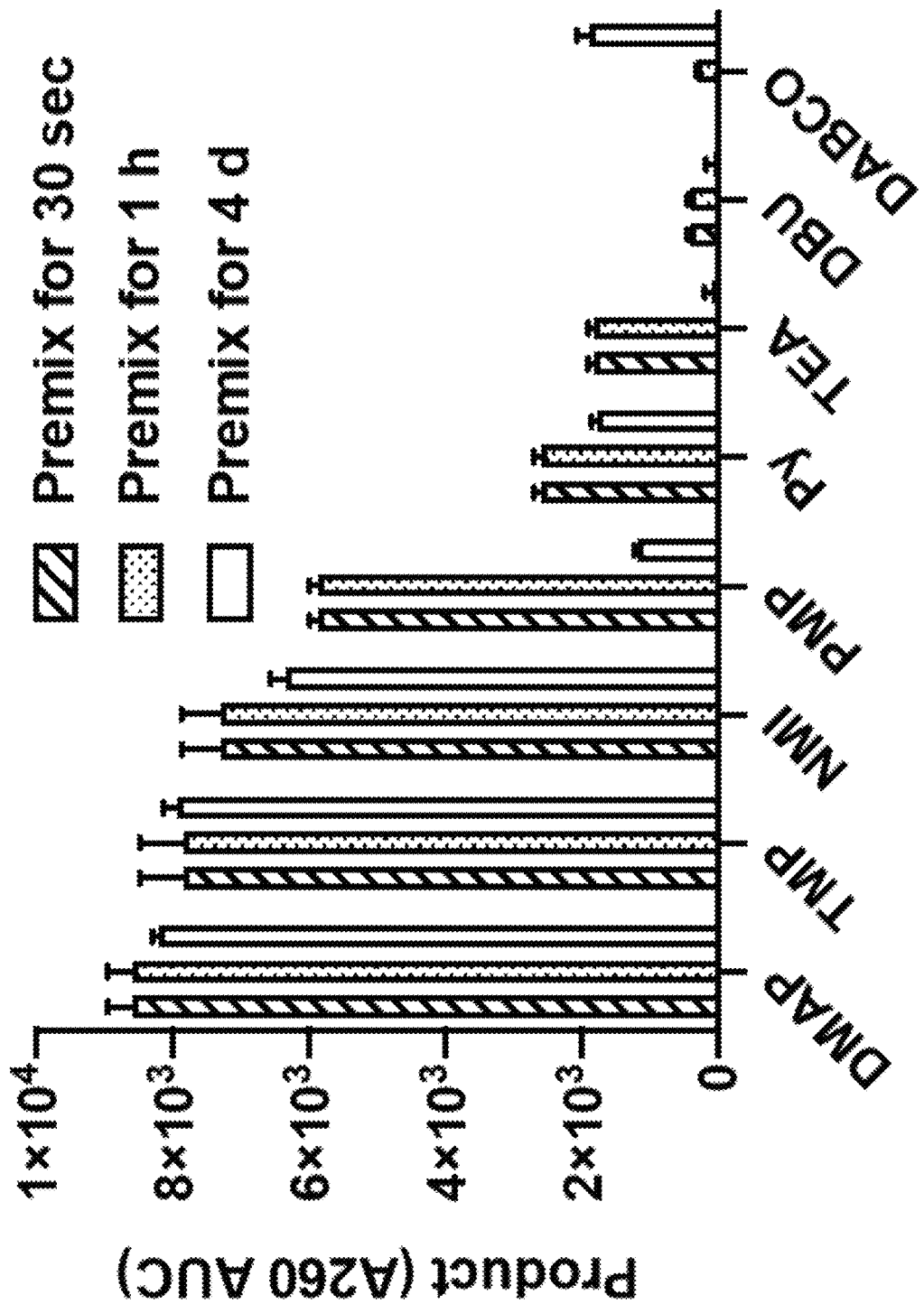
Figure 5B:
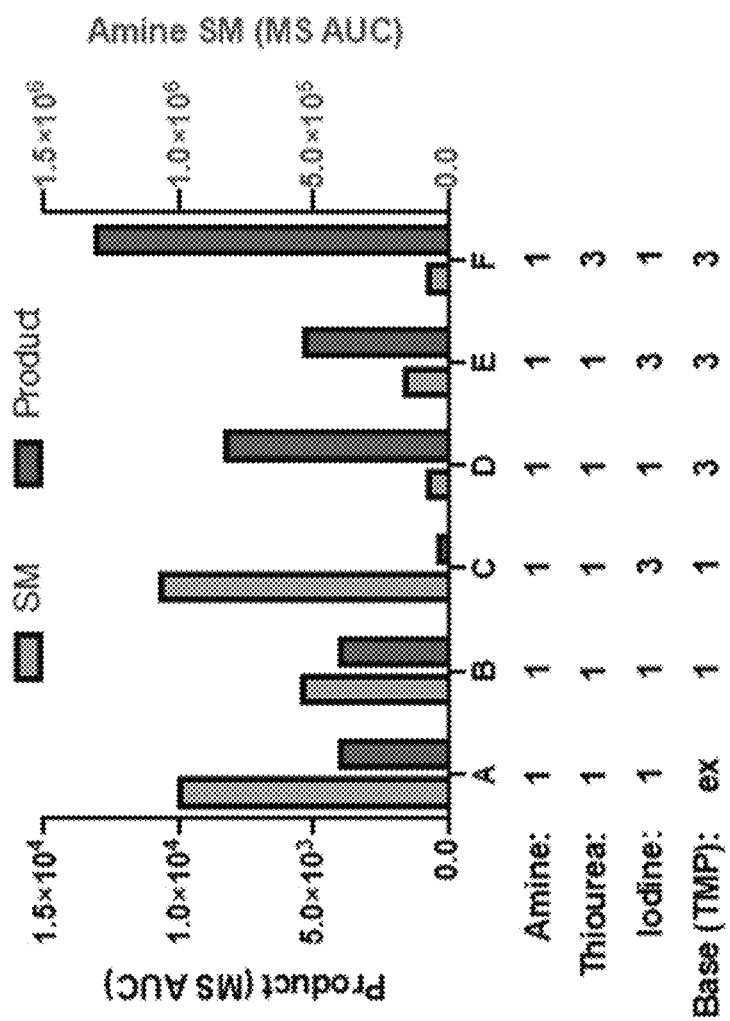
Figure 6A:
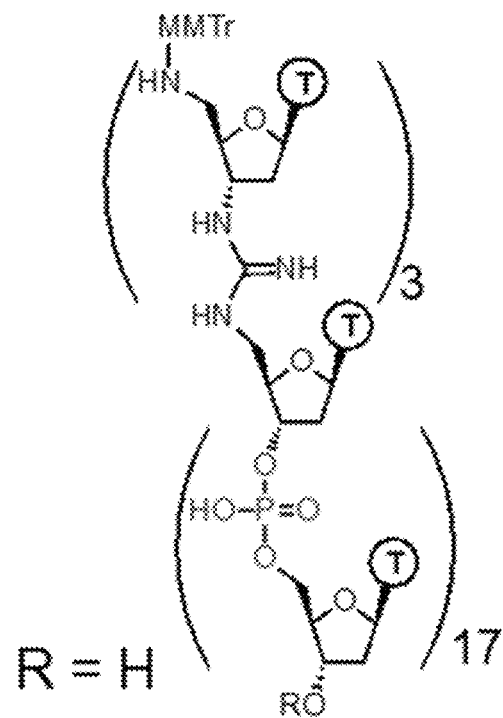
FIGS. 6A and 6B show the confirmation of DNA-DNG mixed strands via MALDI-TOF.
Figure 6B:
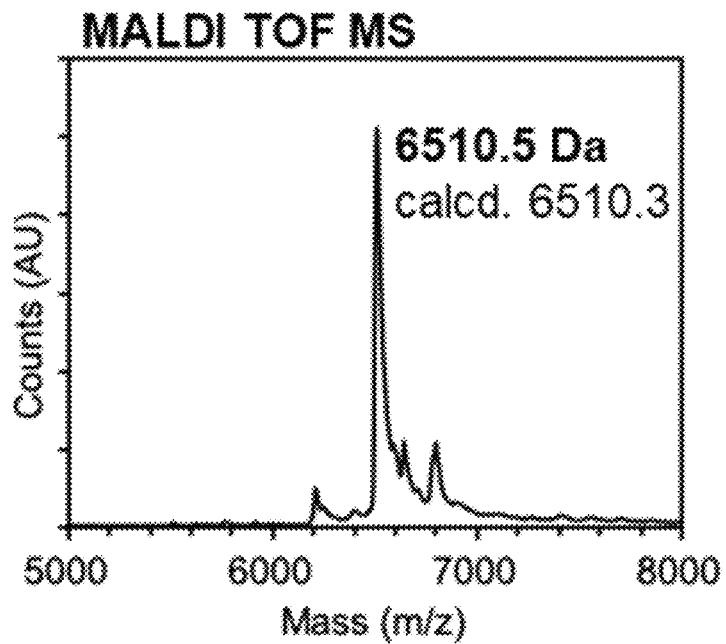
Figure 7A:
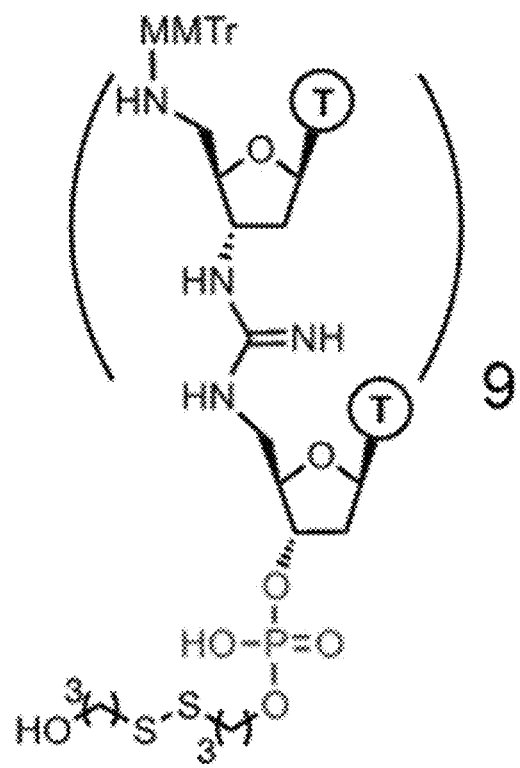
FIGS. 7A-7C show the characterization of primarily DNG-containing strands by MALDI-TOF MS and SDS-PAGE.
Figure 7B:
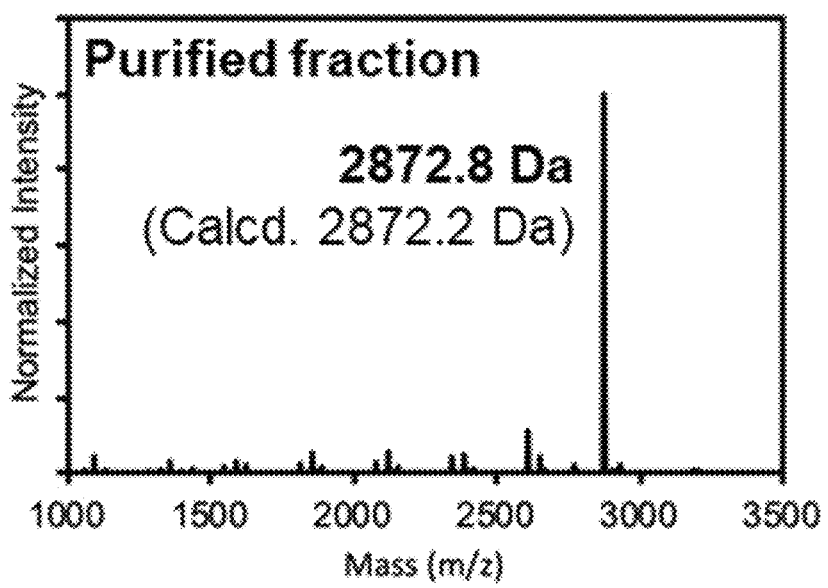
Figure 7C:
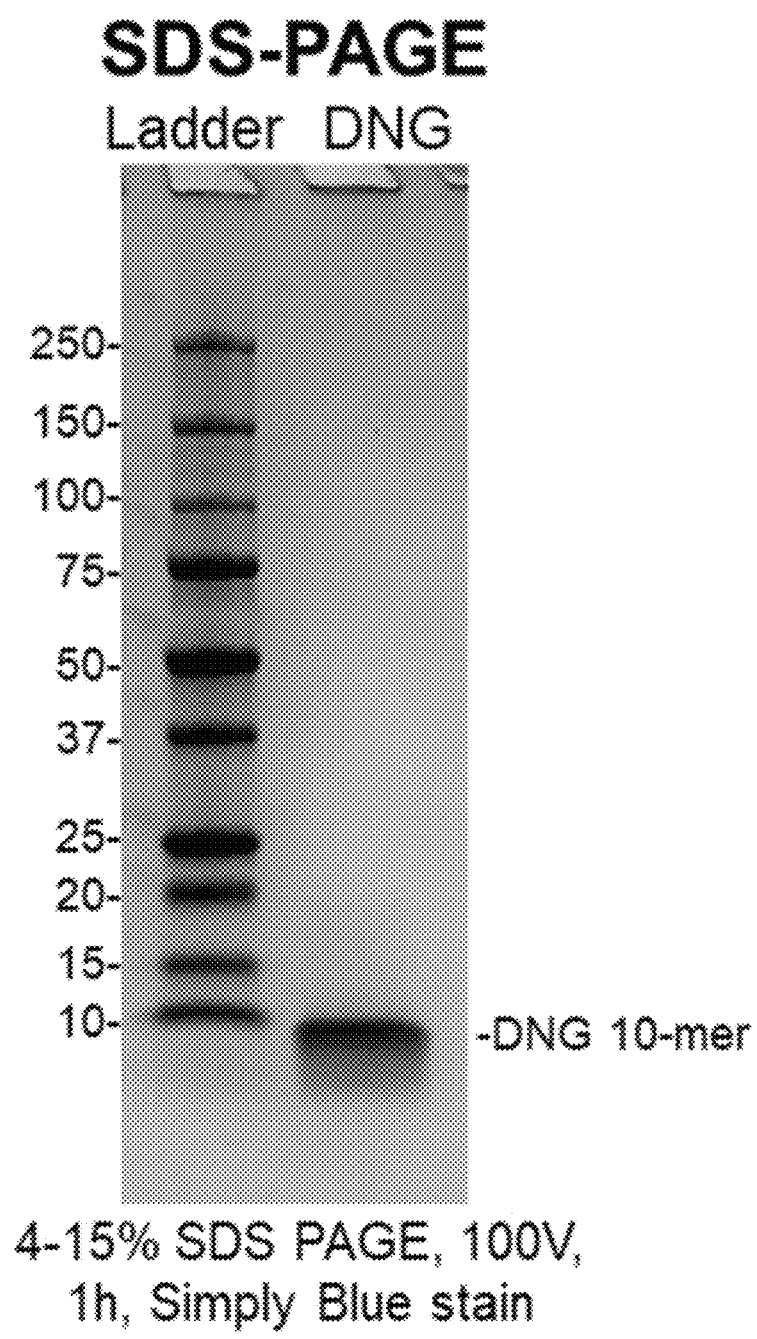
Figures 13, 14:
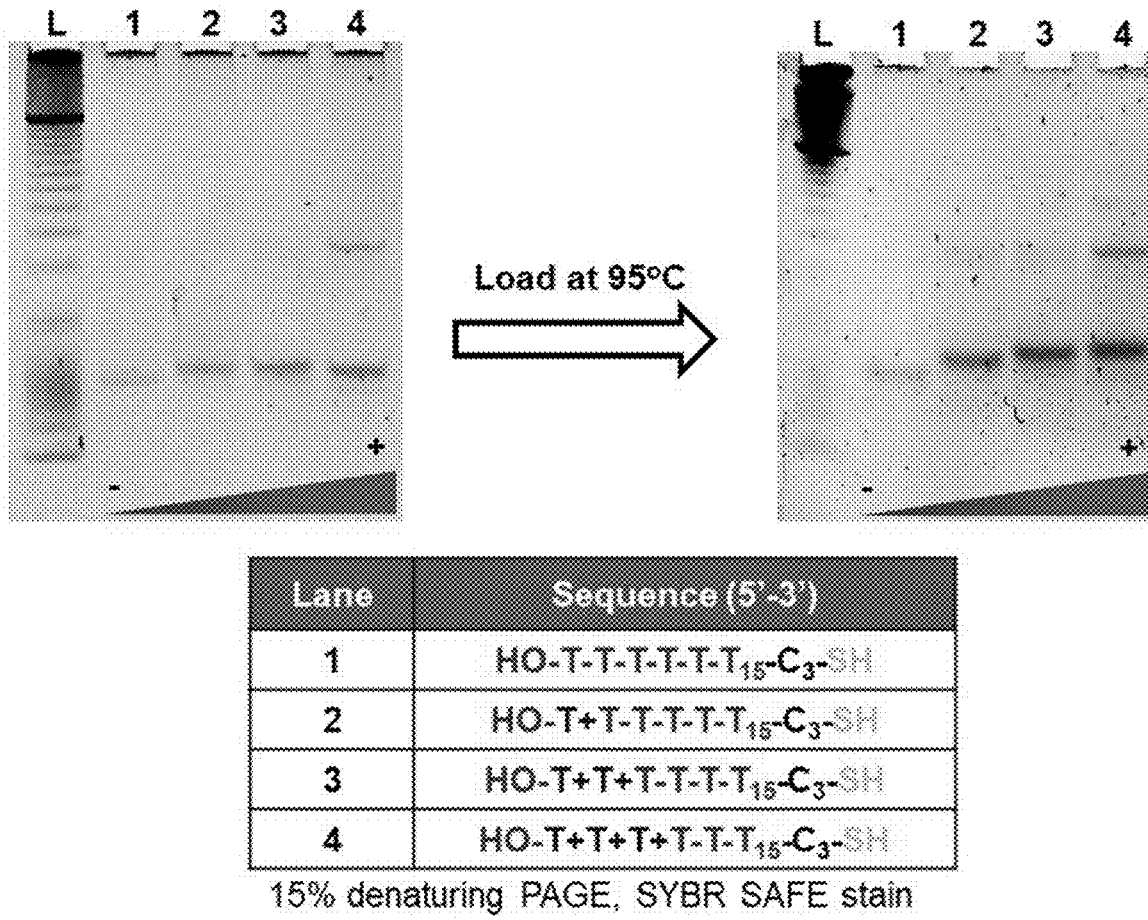
FIG. 13 is an image of an electrophoresis experiment showing that DNG-DNA oligonucleotides as described herein display self-assembly behavior that is denatured at elevated temperatures.
FIG. 14 is a chart showing that the DNA loading density of salt-aged SNAs decreases with an increasing number of positively-charged DNG linkages (DNG loading determined via OliGreen® assay).

Among the advantages of the synthesis methods disclosed herein are the use of non-toxic reagents for synthesis. The methods of the disclosure avoid the use mercury and thiophenol. Further, the methods of the disclosure can be used on an automated oligonucleotide synthesizer (industry standard machine) (see FIG. 1). It has advantageously been found that the synthesis methods disclosed herein can use electrophilic iodine reagents to catalyze DNG oligonucleotide synthesis, instead of toxic and difficult-to-use mercury reagents (see FIG. 2). A variety of electrophilic iodine sources can be used (FIGS. 2 and 3), and it can be advantageous to use molecular iodine (12) (FIG. 2). In the methods disclosed herein, electrophilic iodine reagents are combined with a base to synthesize DNG oligonucleotides (see FIGS. 4 and 5). It can be advantageous to use an organic base having a p$K_a$ of about 7 to about 11 (see FIG. 4). Without being bound by theory, aliphatic α-protons to the amine may cause degradation of the base, and therefore bases without α-protons may be more stable for use in DNG oligonucleotide synthesis (FIG. 4). The exact ratio of reagents is important, and ratios of reagents that lead to higher yields have been identified (see FIG. 5). The reagents (iodine and base (TMP)) can be premixed and are stable up to 24 hours; excess thiourea decreases yield, and 3 equivalents of base results in the highest yields (see FIG. 5). Confirmation of the synthesis and characterization of DNG-containing oligonucleotides can be performed via a variety of methods known to the skilled artisan, including MALDI-TOF and SDS-PAGE (see FIGS. 6, 7, 12, and 13). DNG oligonucleotides show self-assembly (FIG. 13). Without being bound by theory, this behavior is thought to be mediated by ion pairing interactions.

Figure 8:
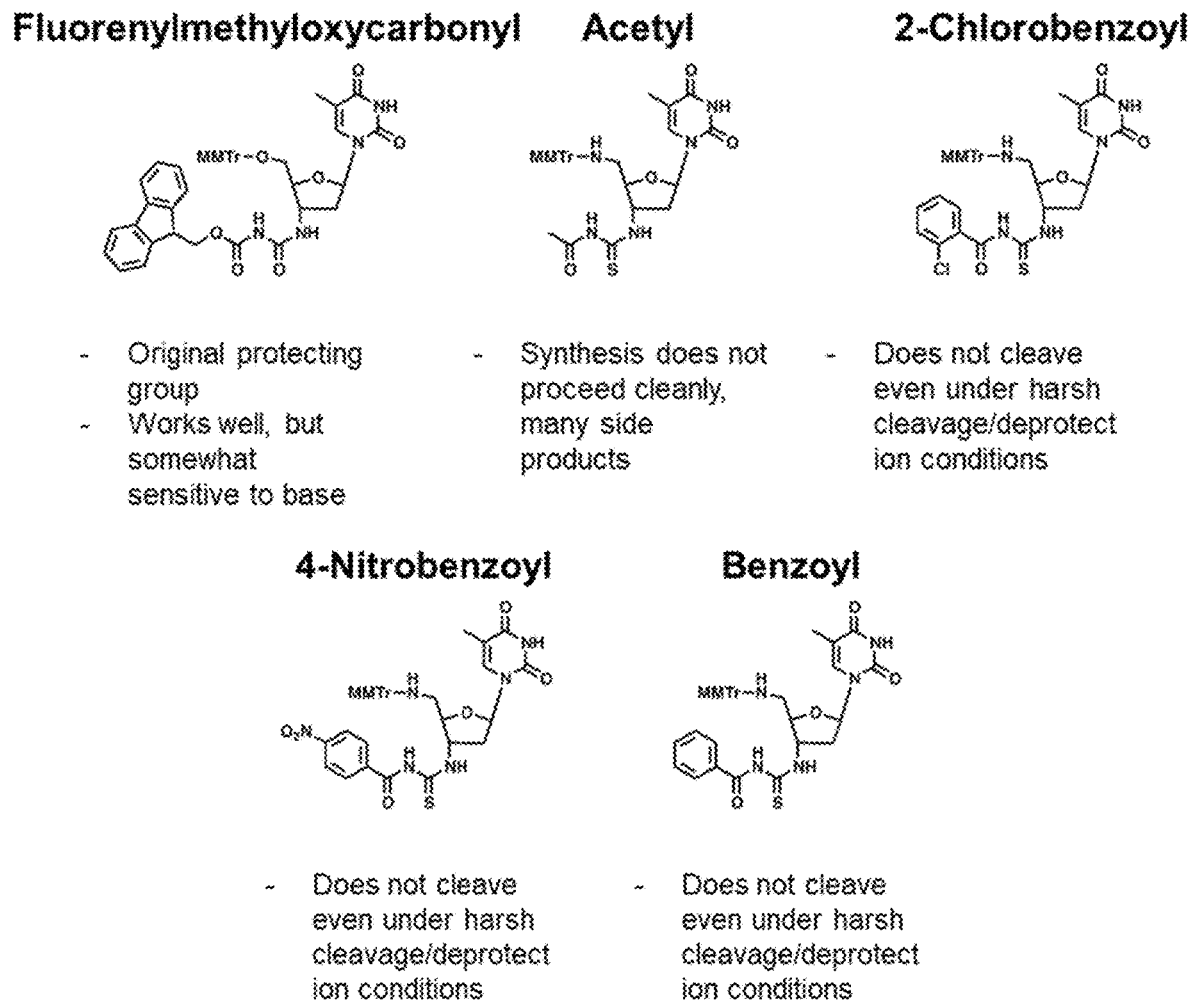
FIG. 8 shows guanidine protecting groups that were explored in the synthesis of DNG-oligonucleotides described herein.
Figure 9B:
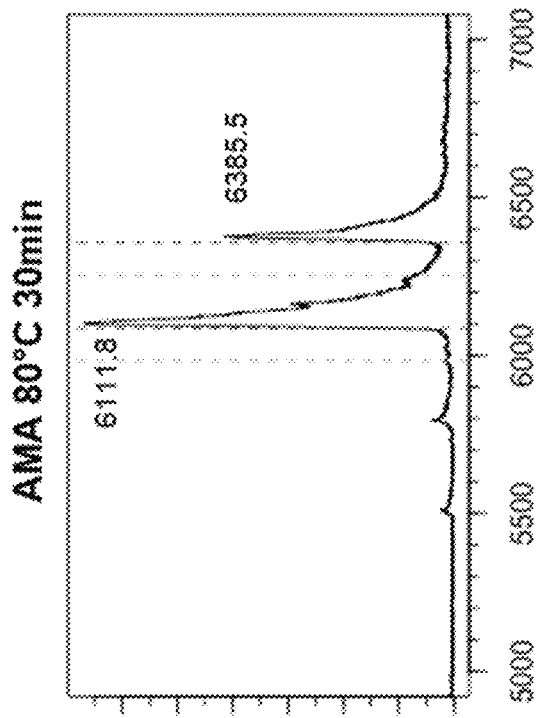
Figure 9A:
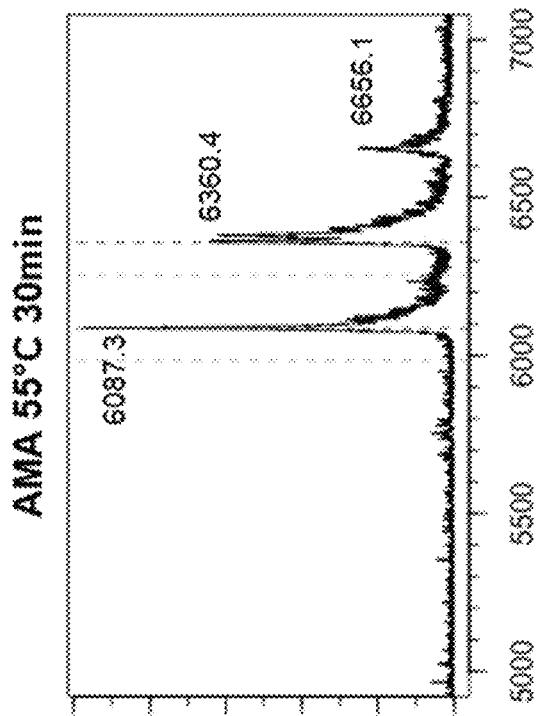
Figure 9D:
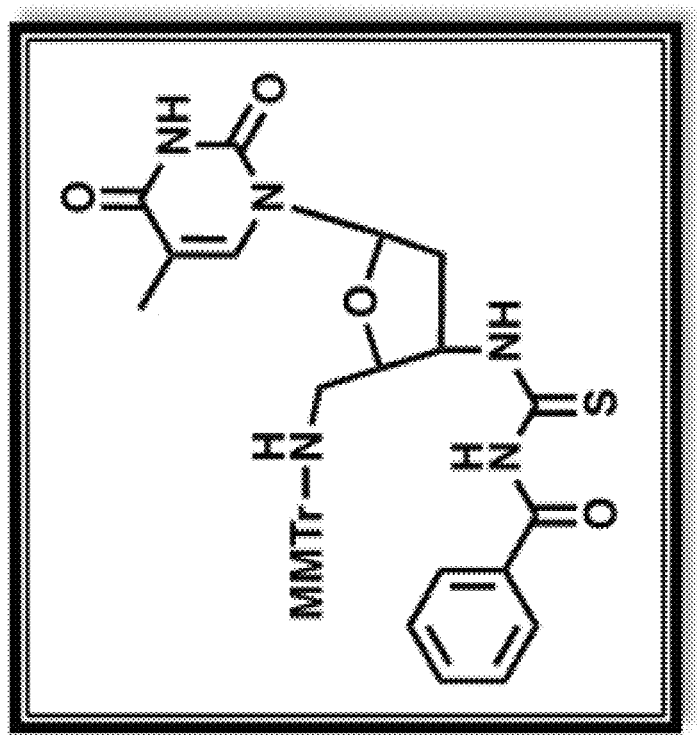
Figure 10:
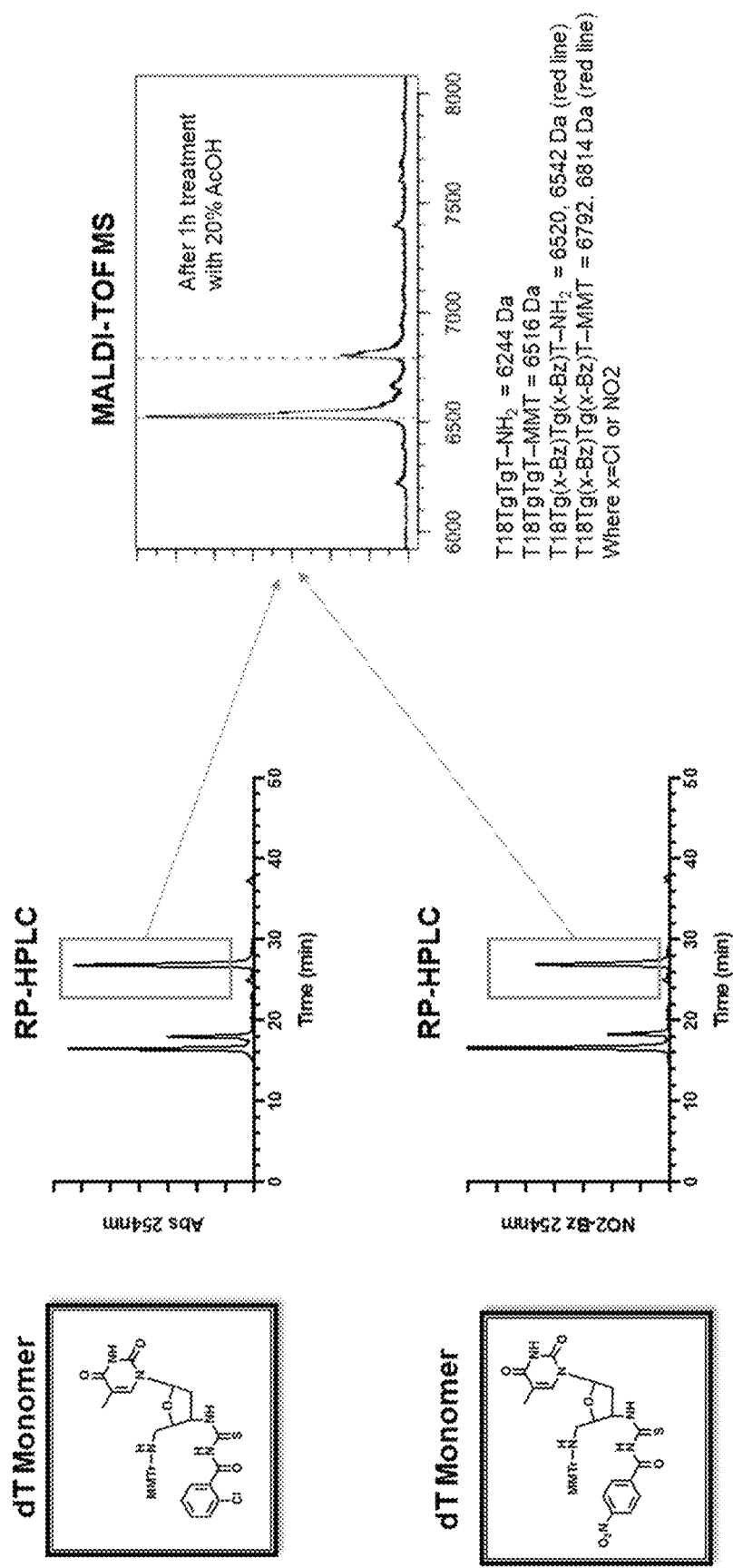
FIG. 10 shows the addition of an electron-withdrawing substituent to a benzoyl-protected DNG nucleoside as disclosed herein does not result in cleavage as detected by HPLC and MALDI-TOF MS.

It can be advantageous in the synthesis of DNG oligonucleotides, including automated syntheses, to protect various functional groups on the starting materials. Suitable protecting groups can be used for sidechain modifications in a variety of applications (e.g., bioconjugation, dyes, ligands, sugars, PEGylation, etc.) In some cases, the thiourea can be protected by a suitable protecting group. For example, the thiourea can be protected by a fluorenylmethyloxycarbonyl (Fmoc), acetyl, 2-chlorobenzoyl, 4-nitrobenzoyl, or benzoyl protecting group (see FIG. 8). It can be advantageous to protect the thiourea with a fluorenylmethyloxycarbonyl (Fmoc) group. It can be advantageous to protect the thiourea with a benzoyl group. Benzoyl protecting groups resist cleavage under alkaline conditions at elevated temperatures (FIG. 9), and addition of electron-withdrawing groups such as chloro or nitro groups does not result in cleavage (FIG. 10).

In some aspects of the disclosure, synthesis of guanidinium-backbone oligonucleotides is realized through the coupling of 3'-thiourea nucleosides with 5'-amino nucleosides using an electrophilic iodine reagent and an appropriate base. Provided are methods for synthesizing a deoxynucleic guanidine oligonucleotide comprising admixing an aminonucleoside with a thiourea nucleoside in the presence of an electrophilic iodine reagent, a base, and a solvent to form a deoxynucleic guanidine oligonucleotide, wherein the base has a p$K_a$ of about 7 to about 11, lacks α-protons, or both. In some cases, the iodine source comprises hydroxyl tosyloxy iodobenzene (HTIB), 2-chloro-1-methyl-pyridinium iodide (CMPI), iodine ($I_2$)/triphenylphosphine, 1,3-diiodo-5,5-dimethylhydantoin (DIH), N-iodosuccinimide (NIS), or iodine ($I_2$). In some cases, the iodine source comprises iodine ($I_2$). In some cases, a reaction to form guanidinium-backbone oligonucleotides as disclosed herein is complete in less than one day, for example, in less than 12 hours, less than 6 hours, less than three hours, less than two hours, less than one hour, or less than 30 minutes. In some cases, the reaction is complete in less than one hour. In some cases, the reaction is complete in 30 minutes.

In some cases, the base has a p$K_a$ of about 7 to about 11 or lacks α-protons. In some cases, the base has a p$K_a$ of about 7 to about 11 and lacks α-protons. In some cases, the base has a p$K_a$ of about 7 to about 11. In some cases, the base has a p$K_a$ of about 7. In some cases, the base has a p$K_a$ of about 8. In some cases, the base has a p$K_a$ of about 9. In some cases, the base has a p$K_a$ of about 10. In some cases, the base has a p$K_a$ of about 11. In some cases, the base lacks α-protons. In some cases, the base comprises pyridine, N-methylimadazole (NMI), N,N-dimethylaminopyridine (DMAP), 2,2,6,6-tetramethylpiperidine (TMP), triethylamine (TEA), 1,2,2,6,6-pentamethylpiperidine (PMP), 1,8-diazabicyclo[5.4.0]undec-7-ene (DBU), or 1,4-diazabicyclo[2.2.2]octane (DABCO). In some cases, the base comprises N,N-dimethylaminopyridine (DMAP) or 2,2,6,6-tetramethylpiperidine (TMP). In some cases, the base comprises N-methylimadazole (NMI), N,N-dimethylaminopyridine (DMAP), 2,2,6,6-tetramethylpiperidine (TMP), triethylamine (TEA), 1,2,2,6,6-pentamethylpiperidine (PMP), or 1,4-diazabicyclo[2.2.2]octane (DABCO). In some cases, the base comprises N,N-dimethylaminopyridine (DMAP) or 2,2,6,6-tetramethylpiperidine (TMP).

In some cases, the ratio of base to electrophilic iodine is about 4:1. In some cases, the ratio of base to electrophilic iodine is about 3:1. In some cases, the ratio of base to electrophilic iodine is about 2:1. In some cases, the ratio of base to electrophilic iodine is about 1:1.

In some cases, the thiourea nucleoside is present in an about 3:1 ratio with respect to the electrophilic iodine. In some cases, the thiourea nucleoside is present in an about 2:1 ratio with respect to the electrophilic iodine. In some cases, the thiourea nucleoside is present in an about 1:1 ratio with respect to the electrophilic iodine. In some cases, the thiourea nucleoside is present in an about 0.5:1 ratio with respect to the electrophilic iodine.

In any of the aspects or embodiments of the disclosure, the entire coupling process can be carried out on a standard oligonucleotide synthesizer (e.g., MerMade 12) with minimal alterations.

The methods provided by the disclosure also allow for the synthesis of guanidinium-backbone oligonucleotides at scale for pre-clinical and clinical applications.

EXAMPLES

DNG oligonucleotides were synthesized as described in Skakuj et al, Curr. Protoc. Nucleic Acid Chem. 2020, 81 (1), incorporated herein by reference.

Synthesis of DNG Strands

The automated synthesis of DNG or 5'-DNG-DNA-3' oligonucleotides was carried out using a DNG-enabled MerMade 12 oligonucleotide synthesizer. This protocol was validated using initiator-functionalized CPG beads and thiourea monomers whose syntheses are reported in the literature (see Challa et al., Bioorganic & Medicinal Chemistry, 12(6), 1475-1481.) Without wishing to be bound by theory, the initiator-functionalized CPG provided the primary amine functional group necessary to couple with the thiourea monomer upon activation with an iodine-base complex and produce a protected guanidine internucleoside linkage. This coupling chemistry can proceed in an automated manner and has enabled the synthesis of DNG oligonucleotides up to 20 bases in length and 5'-DNG-DNA-3' chimeras of various ratios. Guanidine-backbone enabled synthesis instruments can routinely achieve 95% coupling yield per step (see Skakuj et al., 2019 Journal of the American Chemical Society, 141(51), 20171-20176).

The activator solution was prepared by combining 126.9 mg (0.50 mmol) of solid iodine and 9.75 mL of anhydrous DCM into a vial to make a 50 mM iodine solution. To this solution was added 253 µL of TMP. This solution is light sensitive and was found to decompose over time, so it was stored wrapped in aluminum foil and used within 24 h.

The thiourea monomer solution was prepared by combining 79.4 mg (0.10 mmol) of thiourea monomer (see Supporting Protocol 2) with 2 mL of DCM followed by 2 mL acetonitrile, for a final solution of 25 mM in 1:1 ACN/DCM.

Automated Synthesis

The activator and thiourea monomer solutions were attached to the synthesizer appropriate positions. The lines were primed with activator and thiourea monomer, a column was loaded with initiator-functionalized CPG, and a synthesis program was run. DNG coupling efficiency was assessed by UV-Vis spectroscopy using the MMTr cleavage method.

Cleavage and Deprotection of Oligonucleotides

When the synthesis had finished (20 min per DNG coupling at the 1 pmol scale or 30 min per DNG coupling at the 5 µmol scale), the solid support beads were dried under vacuum for a few seconds to remove solvent leftovers from the synthesis. The solid support carrying the oligonucleotide product was transferred to a vial, to which was added a 1:1 solution of 40% aqueous ammonia and 40% aqueous methylamine (AMA) (approximately 1 mL for a 1 µmol or 3 mL for a 5 µmol scale synthesis). The capped vial was placed in a 55° C. oven for 30 min, then removed from the oven and allowed to cool for a few minutes prior to opening. Tris buffer was added the vial to a concentration of approximately 0.1 M, and a gentle stream of nitrogen was used to evaporate the ammonia and methylamine.

Purification by PAGE

Oligonucleotides containing more than 30% DNG tend to adsorb onto CPG beads and must be extracted using acid. For these oligonucleotides, a 1 mL 20% acetic acid solution was added to the solid support to reconstitute the oligonucleotide, and the solution was filtered through a 0.2 µm syringe filter.

If PAGE purification was desired, the appropriate protocol was followed (standard denaturing PAGE as described in e.g., Albright & Slatko, Current Protocols in Human Genetics, 00(1), A.3F.1-A.3F.4.) if negatively charged, or using AU PAGE (see AU PAGE protocol below) if cationic.

Purification by HPLC

Strands that are <30% DNG in length were purified using trityl-ON reverse-phase HPLC protocols as described previously (see e.g., Sinha & Jung, Current Protocols in Nucleic Acid Chemistry, 61(1), 10.15.11-10.15.39.). These samples were prepared by adding distilled water to the solid support to reconstitute the oligonucleotides, and filtering through a 0.2 µm syringe filter.

Purification by Simple Extraction

Certain lengths of DNG-only oligonucleotides were purified by a simple extraction protocol based on the adsorption of long DNG strands to glass surfaces compared to shorter failure strands. This method was found to be effective for DNG oligonucleotides around 10 bases in length. Briefly, the solid support was washed 2× with deionized water (1 mL for a 1 µmol scale synthesis), 20% acetic acid was added to the solid support beads (0.5 mL for a 1 µmol scale synthesis) to solubilize the full length DNG product strands, the acetic acid solution was filtered through a 0.2 µm syringe filter, lyophilized to remove acetic acid, and reconstituted in 1 mL deionized water.

Example 2

Purification of DNG Strands Using Preparative Acetic Acid Urea (AU) PAGE

Figure 3A:
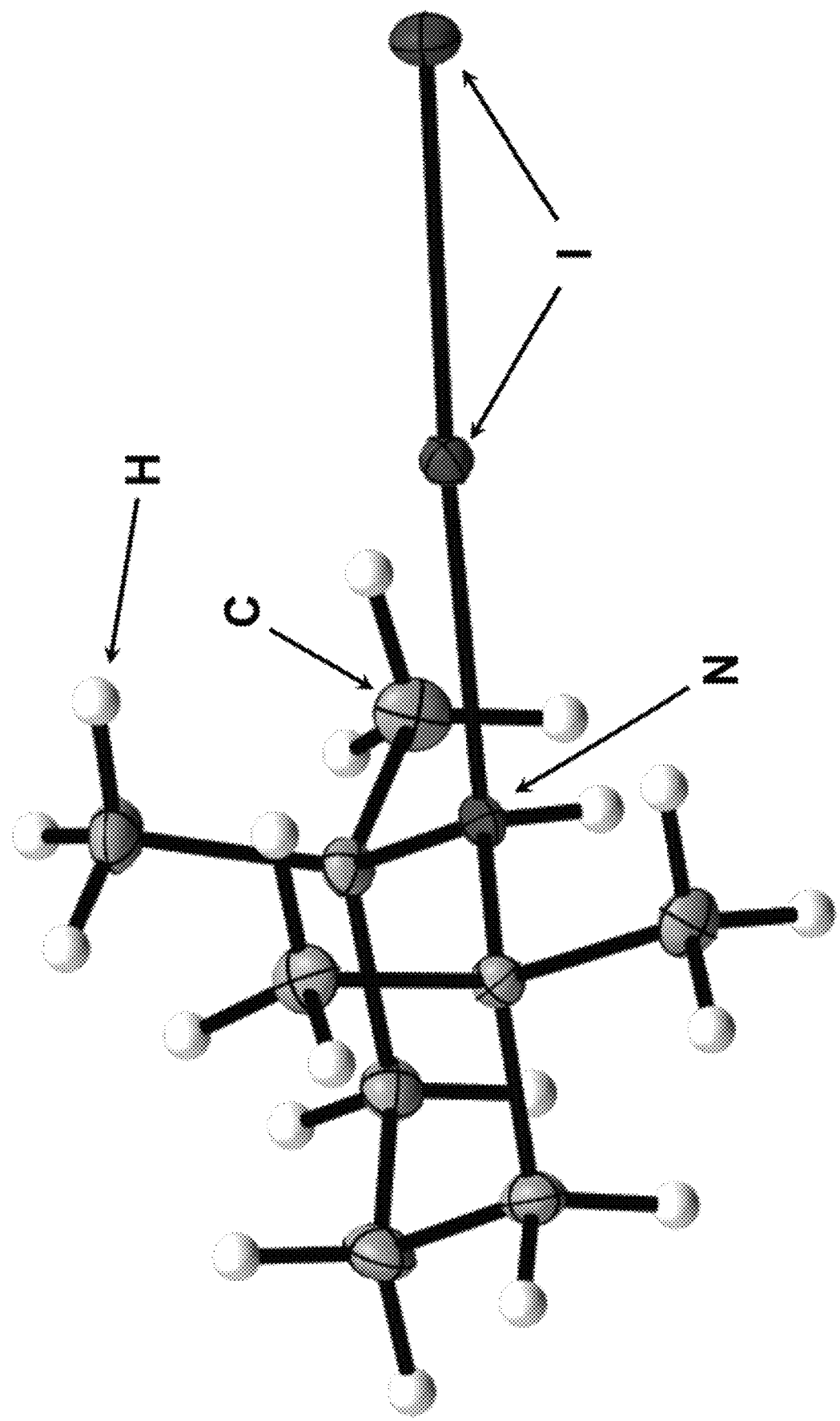
FIG. 3A shows the crystal structure of precipitate material at the bottom of a vial containing iodine/TMP.

AU PAGE can be used to achieve single nucleotide separation of DNG strands for characterization and purification (FIG. 3a). In this protocol readers will purify oligonucleotides using preparative AU PAGE.

Casting the Gel 50 mL of a 24% acetic acid-urea acrylamide solution was prepared by mixing 18 g of urea, 30 mL of 40% acrylamide (19:1 acrylamide:bisacrylamide) solution and 2.5 mL glacial acetic acid. This mixture was sonicated until fully dissolved (40 kHz, 3 min), then adjusted in volume to 50 mL with deionized water. To this solution was added 150 mg ammonium persulfate and 300 μL TEMED in succession, mixing thoroughly between each addition to initiate polymerization. The mixture was sonicated briefly to remove bubbles (40 kHz, 10 s), then cast between gel plates, installing a 10-well comb. The gel was allowed to polymerize for 10 min, then the comb was removed, wells were washed with water, and installed in gel box using 5% acetic acid as running buffer.

Running the Gel

A DNG strand (0.5 μmol synthesis) was resuspended in 100 μL 5% acetic acid, and to this was added 100 μL of 8 M urea and 5% acetic acid solution. The solution was mixed, heated to 95° C. for 5 min, and then loaded over 3 wells while hot.

In a separate well was loaded 20 μL 0.6% methyl green and 50% glycerol solution as loading dye. The gel was run at 250 V for 3.5 h with reversed polarization, until the loading dye reached the bottom of the gel. Reversed polarization was used for oligonucleotides and DNG-DNA chimeras that are expected to carry an overall positive charge (i.e. the number of DNG linkages should be superior to the number of phosphate linkages).

Extracting the DNG Strands from the Gel

The gel was separated from the plates and imaged on plastic wrap over a silica plate with fluorescent indicator using a UV lamp. The desired bands were excised using a razor blade into a 15 mL conical tube, and the gel was finely crushed. 6 mL 5% acetic acid solution was added, and the mixture was incubated at 55° C. with mixing for 16 h.

The gel was pelleted by centrifugation (2000 rcf, 4 min) and the supernatant was collected into a separate conical tube. 2 mL 5% acetic acid was added to the gel fragments, and this mixture was centrifuged again, collecting the supernatant in the same tube. The supernatant was lyophilized and resuspended in 1 mL 5% acetic acid.

The oligonucleotide was desalted using a NAP-10 column pre-equilibrated with 5% acetic acid, according to the manufacturer's protocol. The oligonucleotide solution was then lyophilized and resuspended in 1 mL deionized water. Concentration was measured using absorbance at 260 nm and extinction coefficients calculated from DNA strands of equivalent lengths. The oligonucleotides were stored at 4° C. at concentrations in the 10-100 μM range.

Analytical AU PAGE

If analysis by AU PAGE was desired, after the gel is run it was destained in deionized water overnight and imaged on gel scanner.

Example 3

Characterization of DNG Strands Using MALDI-MS

Successful synthesis of DNG strands can be routinely verified using MALDI-MS. Generally, DNG-rich oligonucleotides need to be deposited in higher amounts on the plate and produce stronger signal in positive mode, as opposed to DNA samples. The presence of acetic acid during deposition also results in superior signal.

Preparation of the DHAP Matrix for MALDI

To a plastic tube were added 25 mg of 2',6'-dihydroxyacetophenone, 300 μL methanol, and dd 111 μL saturated ammonium citrate. A precipitate was produced; the supernatant was used in subsequent steps.

For Anionic Oligonucleotides Containing DNG Linkages 0.3 μL of DNG-modified oligonucleotide were spotted onto a MALDI plate, then 0.3 μL DHAP matrix were added onto the sample and allowed to dry completely (5 min). Purity of the oligonucleotide was assessed using a MALDI source in negative mode.

For Cationic Oligonucleotides Containing DNG Linkages

An aliquot of the DNG-containing oligonucleotide to be analyzed was reconstituted at 100 μM in 20% acetic acid. 2 μL of this solution was dropped onto a MALDI plate, followed by 0.2 μL DHAP matrix, and allowed to dry completely (5 min). Purity of the oligonucleotide was assessed using a MALDI source in positive mode.

Example 4

Synthesis of Initiator-Functionalized CPG

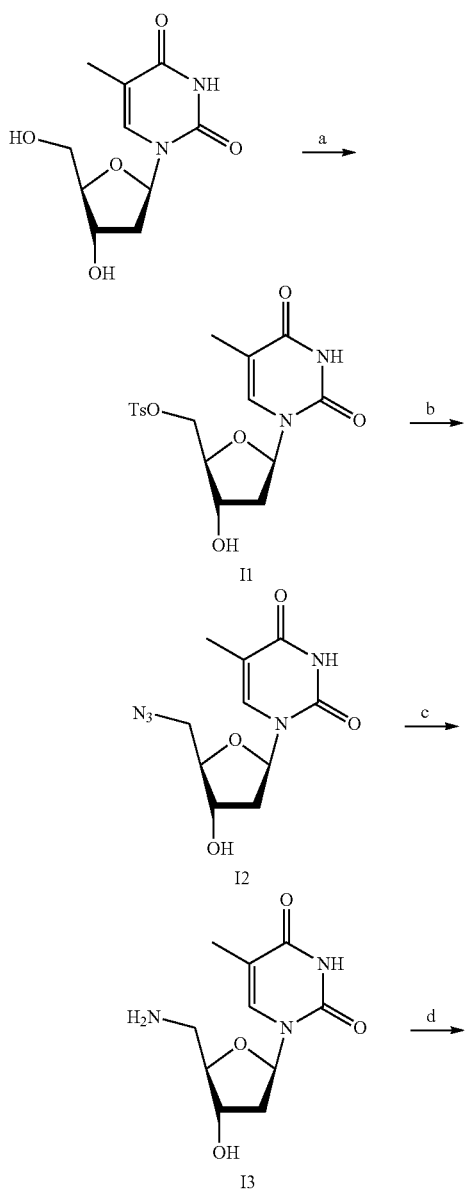

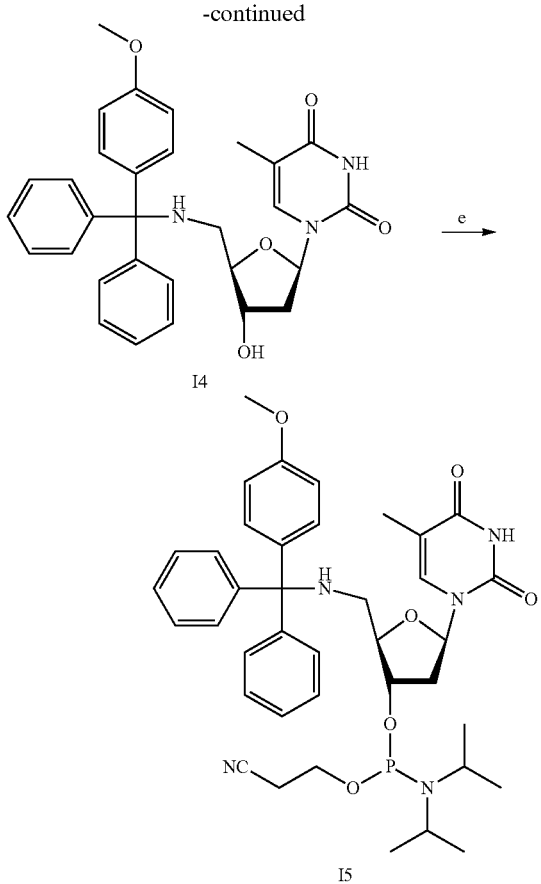

I4

I5

This synthetic sequence is based upon published literature with modifications (Challa & Bruice, 2004). 15 is then coupled to a CPG solid support bearing a 5' hydroxyl or O-DMT group and then acts as the initiator for DNG synthesis.

Synthesis of I1

Thymidine (5 g, 20.7 mmol, 1 equiv.) was combined with pyridine (35 mL) in a flask and stirred to dissolve. The solution was cooled to 0° C. in an ice bath. To this solution was added p-toluenesulfonyl chloride (4.54 g, 23.7 mmol, 1.15 equiv.) in pyridine (5 mL) dropwise over 10 min. The solution was allowed to warm to room temperature while stirring. The solution was poured into ca. 200 mL of cold distilled water, and the precipitate was filtered and washed with water and diethyl ether to yield 11.

Synthesis of I2

I1 (6.4 g, 16.1 mmol, 1 equiv.), sodium azide (1.17 g, 17.9 mmol, 1.1 equiv.), and sodium iodide (0.24 g, 1.61 mmol, 0.1 equiv.) were combined in anhydrous DMF (30 mL) and stirred to dissolve. The reaction was heated to 110° C. under nitrogen for 1 h while stirring, then cooled to room temperature while stirring. The solution was filtered, the solvent removed, and the residue purified by silica gel chromatography with a DCM to 30% methanol gradient to yield 12.

Synthesis of I3

I2 (0.5 g, 1.87 mmol) was combined with 20 mL of methanol. The solution was degassed with argon or nitrogen, and then Pd/C (100 mg) in a slurry with 2 mL of water was added. Hydrogen gas was slowly bubbled (approx. 1 bubble per second) through the solution until all starting material was consumed. Once the reaction was complete, hydrogen gas flow was stopped and the solution was flushed by bubbling argon or nitrogen through the solution for 15 min. The reaction mixture was filtered through a plug of Celite and washed with methanol. The solvent was removed under reduced pressure to yield 13.

Synthesis of I4

I3 (1.35 g, 5.6 mmol, 1 equiv.) was dissolved in 35 mL of pyridine, and triethylamine was added to the solution (0.86 mL, 6.16 mmol, 1.1 equiv.). The solution was cooled to 0° C. in an ice bath while stirring. MMTr-Cl was dissolved in 8 mL of pyridine, and the MMTr-Cl solution was added dropwise over 30 min. The solution was stirred at 0° C. for 2 h, then warmed to room temperature. The solvent was removed under reduced pressure, and the residue was purified using silica chromatography with a DCM to methanol gradient and a constant 5% TEA to yield 14.

Synthesis of I5

This reaction was performed under an inert atmosphere. 14 (0.80 mg, 1.6 mmol, 1 equiv.) was dissolved in DCM (16 mL), to which was added DIPEA (1.0 g, 1.4 mL, 7.8 mmol, 5 equiv.). To this solution was added 2-cyanoethyl N,N,-diisopropylchlorophoshoramidite (1.1 g, 1.0 mL, 4.7 mmol, 3 equiv.), and the mixture was stirred at room temperature for 2 h. The solvent was removed under reduced pressure, and the residue was purified with flash silica chromatography with a 60/40 hexanes/DCM solvent with 5% TEA under inert atmosphere to yield 15.

Coupling of I5 to CPG Support

I5 was resuspended in anhydrous DCM at a concentration of 0.1 M, and coupled to a hydroxyl or O-DMT terminated CPG-filled column via standard phosphoramidite chemistry reagents in an oligonucleotide synthesizer, by following the manufacturer's instructions. Load in the instrument's main chamber.

Example 5

Synthesis of Thiourea Monomer

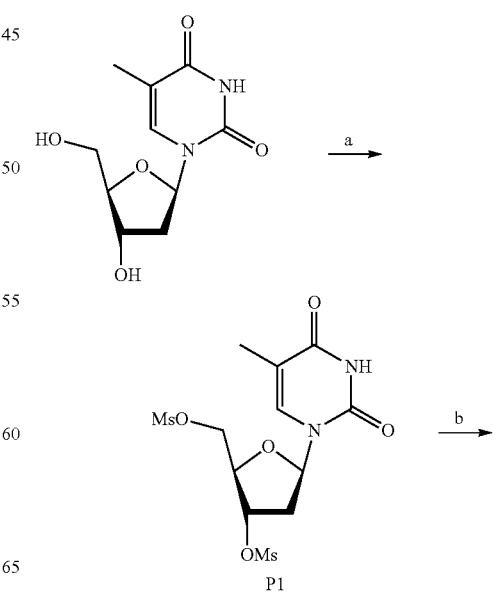

P1

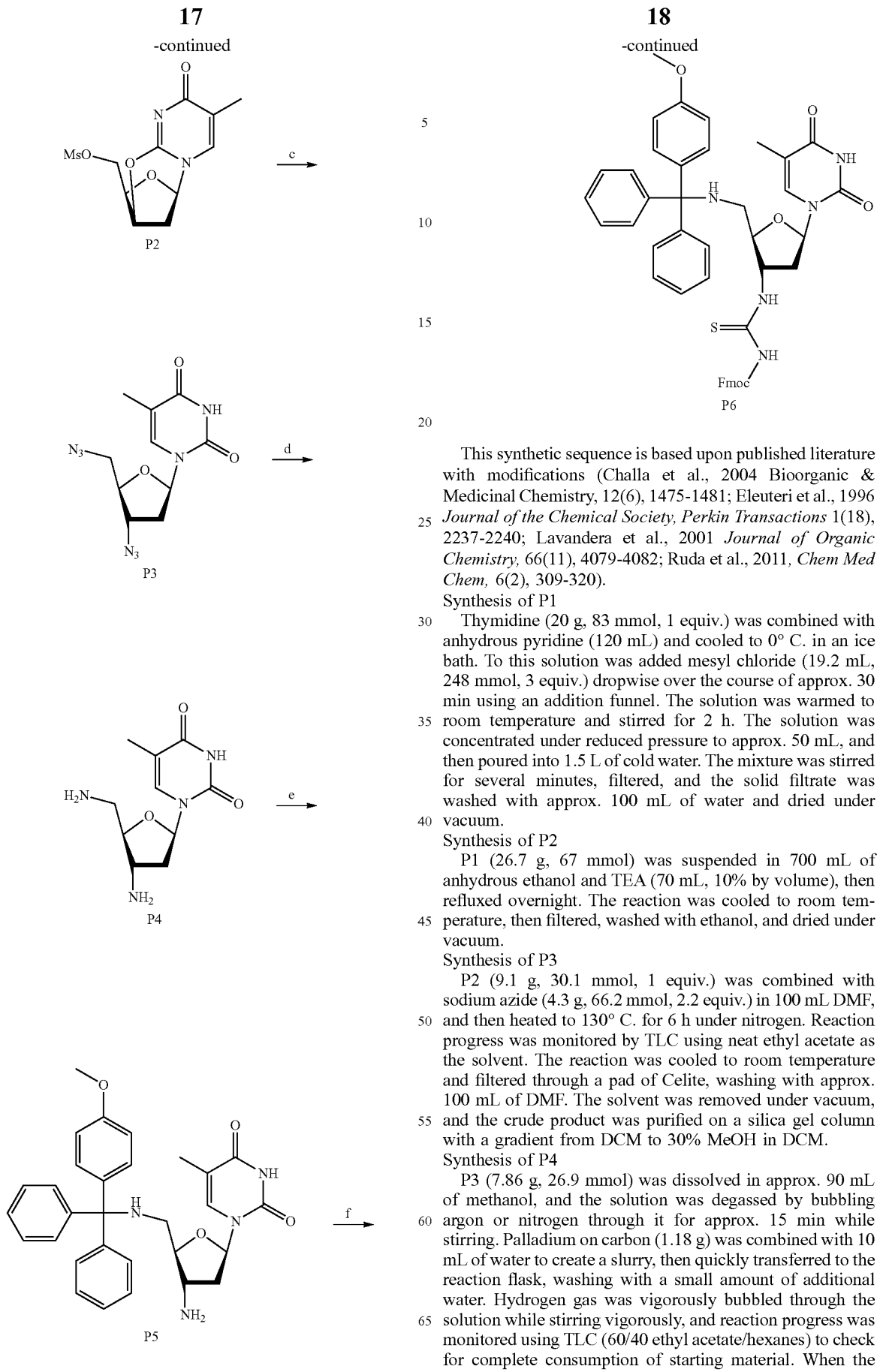

This synthetic sequence is based upon published literature with modifications (Challa et al., 2004 Bioorganic & Medicinal Chemistry, 12(6), 1475-1481; Eleuteri et al., 1996 *Journal of the Chemical Society, Perkin Transactions* 1(18), 2237-2240; Lavandera et al., 2001 *Journal of Organic Chemistry*, 66(11), 4079-4082; Ruda et al., 2011, *Chem Med Chem*, 6(2), 309-320).

Synthesis of P1

Thymidine (20 g, 83 mmol, 1 equiv.) was combined with anhydrous pyridine (120 mL) and cooled to 0° C. in an ice bath. To this solution was added mesyl chloride (19.2 mL, 248 mmol, 3 equiv.) dropwise over the course of approx. 30 min using an addition funnel. The solution was warmed to room temperature and stirred for 2 h. The solution was concentrated under reduced pressure to approx. 50 mL, and then poured into 1.5 L of cold water. The mixture was stirred for several minutes, filtered, and the solid filtrate was washed with approx. 100 mL of water and dried under vacuum.

Synthesis of P2

P1 (26.7 g, 67 mmol) was suspended in 700 mL of anhydrous ethanol and TEA (70 mL, 10% by volume), then refluxed overnight. The reaction was cooled to room temperature, then filtered, washed with ethanol, and dried under vacuum.

Synthesis of P3

P2 (9.1 g, 30.1 mmol, 1 equiv.) was combined with sodium azide (4.3 g, 66.2 mmol, 2.2 equiv.) in 100 mL DMF, and then heated to 130° C. for 6 h under nitrogen. Reaction progress was monitored by TLC using neat ethyl acetate as the solvent. The reaction was cooled to room temperature and filtered through a pad of Celite, washing with approx. 100 mL of DMF. The solvent was removed under vacuum, and the crude product was purified on a silica gel column with a gradient from DCM to 30% MeOH in DCM.

Synthesis of P4

P3 (7.86 g, 26.9 mmol) was dissolved in approx. 90 mL of methanol, and the solution was degassed by bubbling argon or nitrogen through it for approx. 15 min while stirring. Palladium on carbon (1.18 g) was combined with 10 mL of water to create a slurry, then quickly transferred to the reaction flask, washing with a small amount of additional water. Hydrogen gas was vigorously bubbled through the solution while stirring vigorously, and reaction progress was monitored using TLC (60/40 ethyl acetate/hexanes) to check for complete consumption of starting material. When the starting material was consumed, the hydrogen flow was stopped, and argon or nitrogen was bubbled through the solution vigorously for approx. 15 min. The solution was filtered through a pad of Celite, and washed with methanol until the filtrate no longer gave a strong signal on a TLC plate upon UV illumination, and the solvent was removed under vacuum.

Synthesis of P5

P4 (4.21 g, 17.5 mmol, 1 equiv.) was fully dissolved in 350 mL of anhydrous pyridine and 5% triethylamine by volume (approx. 17 mL) and cooled to 0° C. MMTr-Cl (5.42 g, 16.5 mmol, 1 equiv.) was dissolved in 25 mL of anhydrous pyridine, and the MMTr-Cl solution was added dropwise over approx. 30 min while maintaining reaction at 0° C. Once the addition was complete, the reaction was allowed to warm to room temperature for 30 min and stirred for a further 2 h. The solvent was removed under reduced pressure, and the crude reaction mixture was loaded onto Celite using methanol, then eluted using a 0.5/5/94.5 MeOH/TEA/DCM solvent system.

Synthesis of P6

P5 (1.58 g, 2.0 mmol, 1 equiv) was combined in 40 mL of anhydrous DCM with Fmoc-NCS (0.67 g, 2.4 mmol, 1.2 equiv), and the solution was stirred at room temperature for 16 h. The solvent was removed under reduced pressure, and the residue was purified over silica using a DCM to ethyl acetate gradient.

HRMS-ESI (m/z): [M+H]+ calcd for $C_{46}H_{44}N_5O_6S$, 794.3007; found 794.3016.

Example 6

Uptake of DNG Oligonucleotide SNAs by C166 Cells

Figure 11:
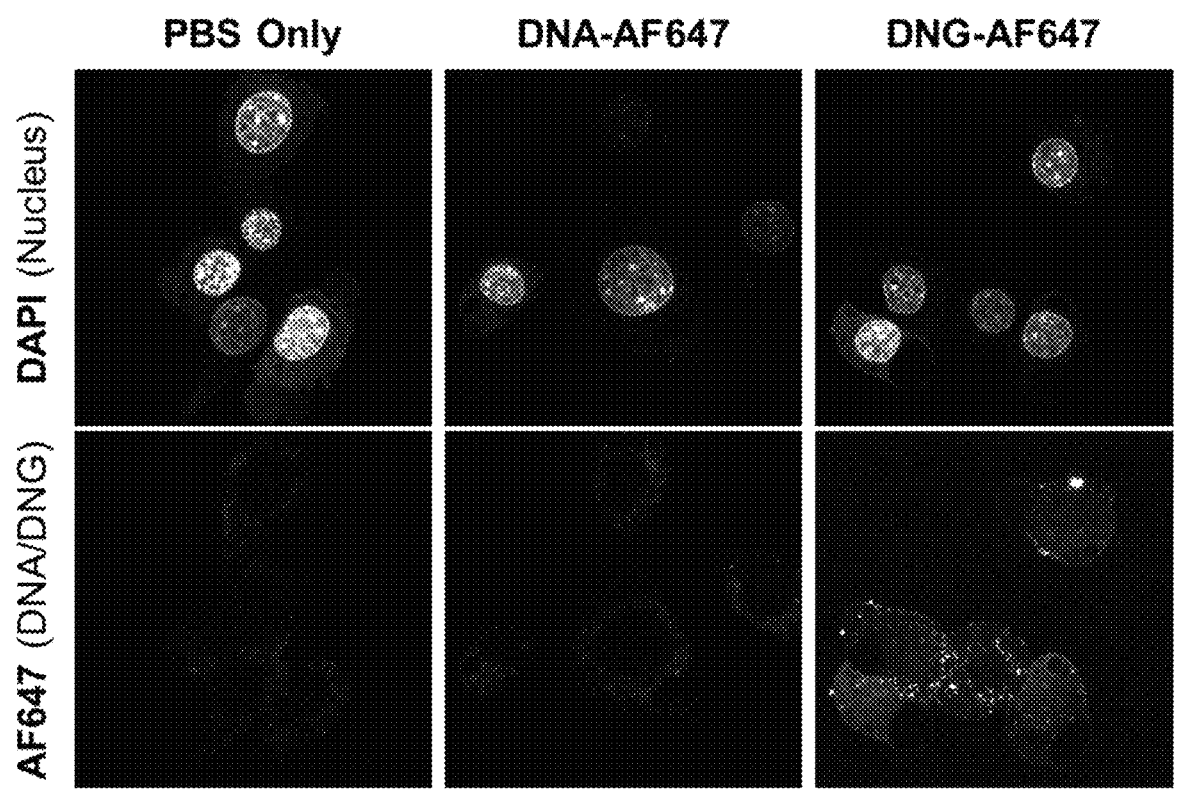
FIG. 11 shows a confocal microscopy image of GFP-expressing C166 cells treated with either PBS alone, an Alexa Fluor 647® (AF647)-labeled DNA oligonucleotide, or AF647-labeled DNG oligonucleotide as described herein. The DNG-oligonucleotides show higher uptake into C166 cells compared to DNA visualized using AF647 fluorescence.

GFP-expressing C166 cells were plated at 100 k/mL in an 8-well chambered cover slip. The cells were treated with PBS, $pT(gT)_9$-AF647 (added as AF647 succinimide ester, comprising 1 standard DNA base on 5' end followed by 9 DNG bases on 3' end to give a 10-mer), or DNA-AF647 (added as AF647-maleimide), both 40 mol % labeled $T_{10}$ (10-mers), at a 600 nM oligonucleotide concentration for 2.5 hours in optiMEM. Cells were fixed and imaged with a confocal fluorescence microscope (see FIG. 11).

Example 7

Synthesis of SNAs Comprising DNG Oligonucleotides (Salt Aging Method)

SNAs were prepared by functionalizing 13-nm citrate-capped gold nanoparticles (AuNPs) with DNA at a ratio of 1000:1 in water for 16 hours. Salt aging was performed with 1% Tween-20 and NaCl from 0 to 0.5 M over 4 hours, and the particles were incubated for another 16 hours prior to washing excess DNA by pelleting. Non-specifically adhered strands were removed using NaCl and urea washes, prior to washing 5× with water. DNA loading was confirmed by OliGreen® assay. It was observed that the loading density of salt-aged SNAs decreased with an increasing number of positively-charged DNG linkages (see FIGS. 14 and 15).

Example 8

Synthesis of SNAs Comprising DNG Oligonucleotides (Freeze-Thaw Method)

DNA:AuNP nanoparticles at 300:1 or 500:1 by volume in water were frozen for 10 minutes on dry ice, then allowed to thaw to room temperature overnight. The particles were washed with water and urea, then 5× with water before characterization by OliGreen® assay. Additional details of the freeze-thaw synthesis method can be found e.g., in Liu et al., J. Am. Chem. Soc. 2017, 139 (28), 9471-9474.

It was observed that the freeze-thaw method led to more consistent DNG-DNA loadings on SNAs (see FIG. 17).

Example 9

Cellular Uptake of SNAs

The effect of position and number of DNG inserts on cellular uptake of SNAs was observed.

SNAs (3 nM by Au) comprising varying numbers and positions of DNG inserts were incubated with HEK293 cells (human embryonic kidney cells) in Opti-MEM™ reduced serum media at 37° C. for 5 hours. Plates were rinsed 3× with phosphate buffered saline (PBS), trypsinized, pelleted, and digested with 2% $HCl/HNO_3$ prior to analysis.

Figure 19A:
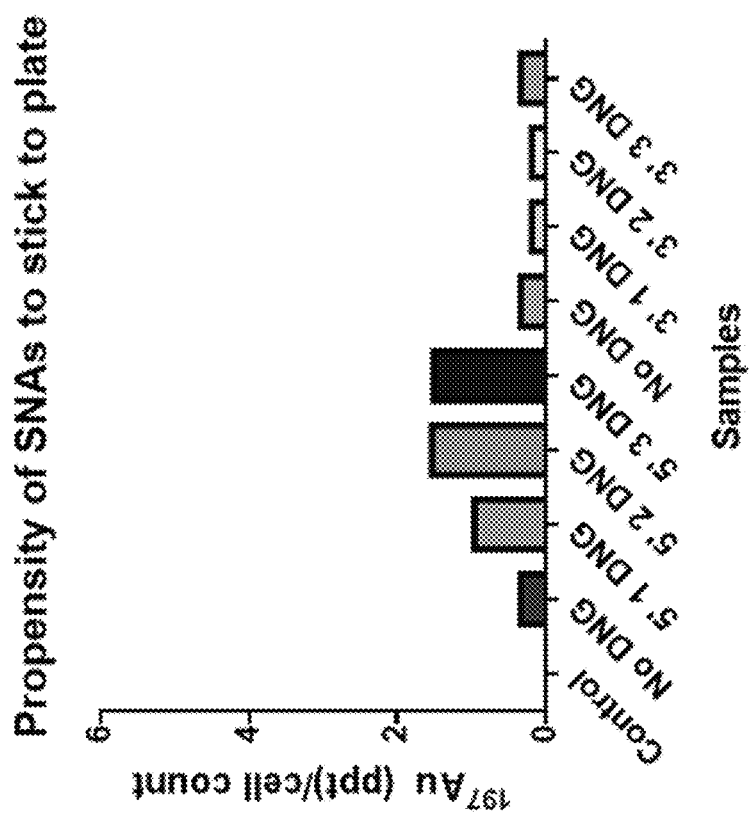
FIG. 19A—is a chart showing cationic DNG inserts increase cellular uptake of SNAs.
Figure 19B:
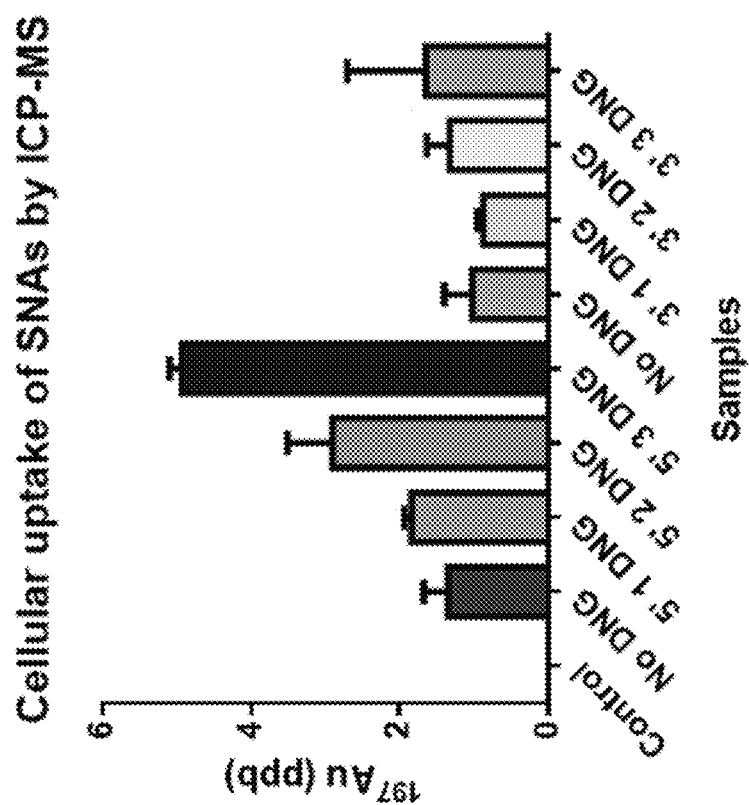
FIG. 19B is a chart showing cationic DNG inserts increase the propensity for SNAs to stick to a well plate.

It was observed that the placement and number of DNG inserts dictate cell uptake: surface modifications (5') of SNAs lead to increased cellular uptake contrary to DNG modifications near the core (3'). Surface modifications (5') also lead to an increased propensity to stick to substrates. (FIG. 19).

SNAs (2.5 nM by Au, 225 nM by DNA with 7.5 nM Cy3 dye) were incubated with C166 cells in Opti-MEM™ reduced serum media at 37 or 4° C. for 2 hours. Plates were rinsed 3× with PBS and fixed with 4% paraformaldehyde.

Figure 20:
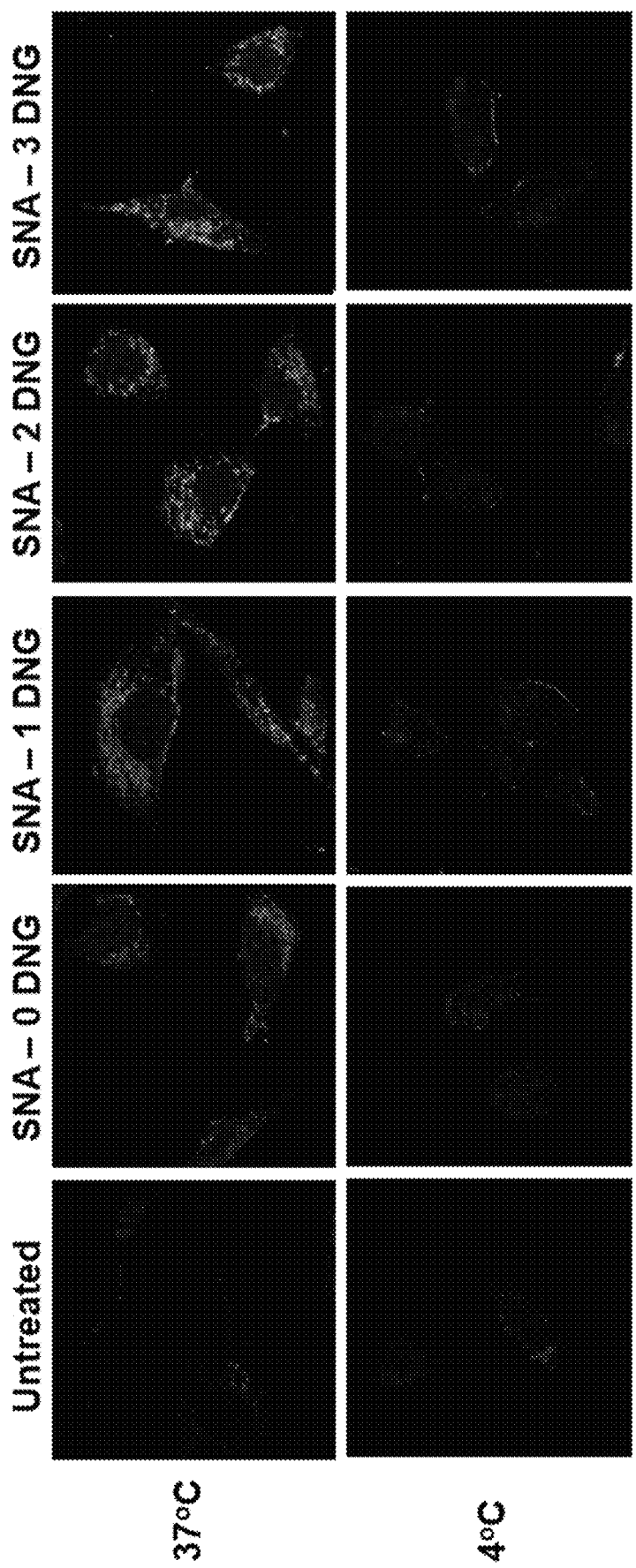
FIG. 20 is a confocal microscopy image showing that increasing the number of surface DNG modifications on SNAs leads to increased cellular uptake in HEK 293 cells under physiological conditions (37° C.) and that the cellular uptake of DNG SNAs is mediated mainly by active processes as illustrated by the decreased fluorescence signal at 4° C. where active transport is shut down. Green: Cy3-labeled SNAs.

FIG. 20 shows confocal microscopy images of these cells, indicating that increasing the number of surface DNG modifications on SNAs leads to increased cellular uptake. Green: Cy3-labeled SNAs, Purple: DAPI nuclear stain.

Figure 21:
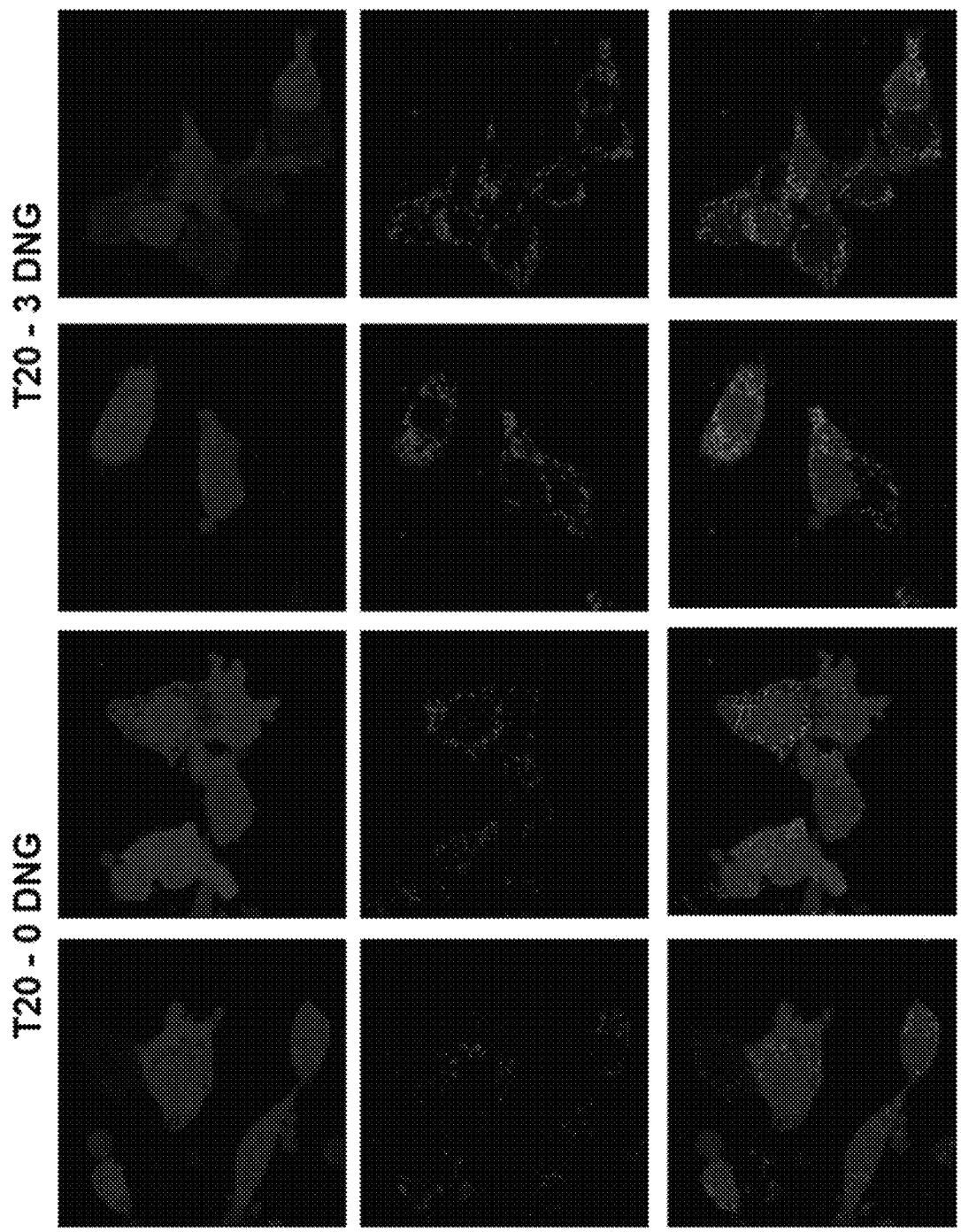
FIG. 21 is a confocal microscopy image showing that increasing the number of surface DNG modifications on SNAs leads to increased cellular uptake in C166-GFP cells under physiological conditions (37° C.). Red: Cy5-labeled SNAs. Green: Constitutively-expressed GFP.

FIG. 21 shows confocal microscopy images of cells incubated at 3 nM by gold in Opti-MEM™ reduced serum media at 37° C. for 2 hours. Plates were rinsed with PBS and fixed with 2% paraformaldehyde. The images indicate that increasing the number of surface DNG modifications on SNAs leads to increased cellular uptake. Green: GFP, Red: Cy5-labeled SNAs.

Figure 22:
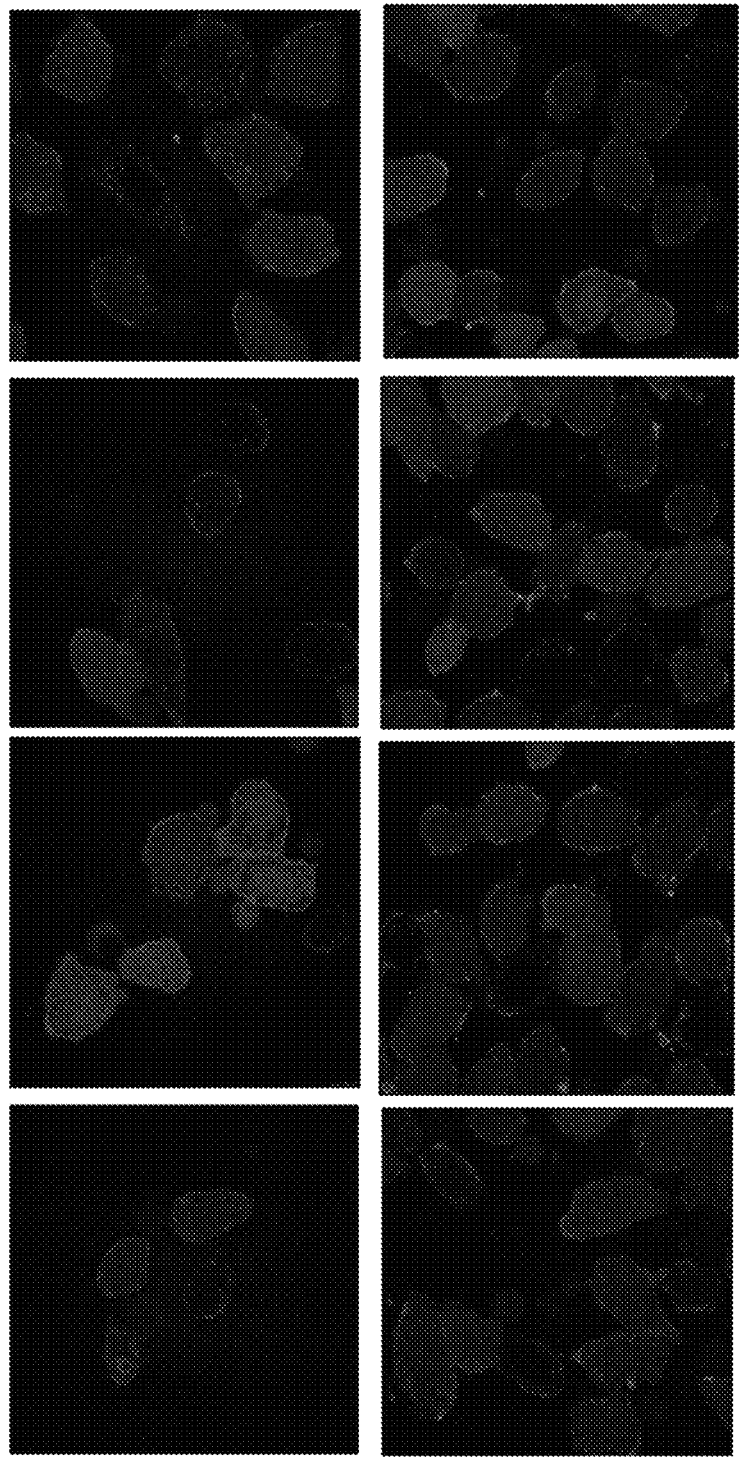
FIG. 22 is a confocal microscopy image showing that increasing the number of surface DNG modifications on SNAs leads to increased cell surface interactions in C166-GFP cells when active transport is shut down (4° C.). Red: Cy5-labeled SNAs. Green: Constitutively-expressed GFP.
Figure 23A:
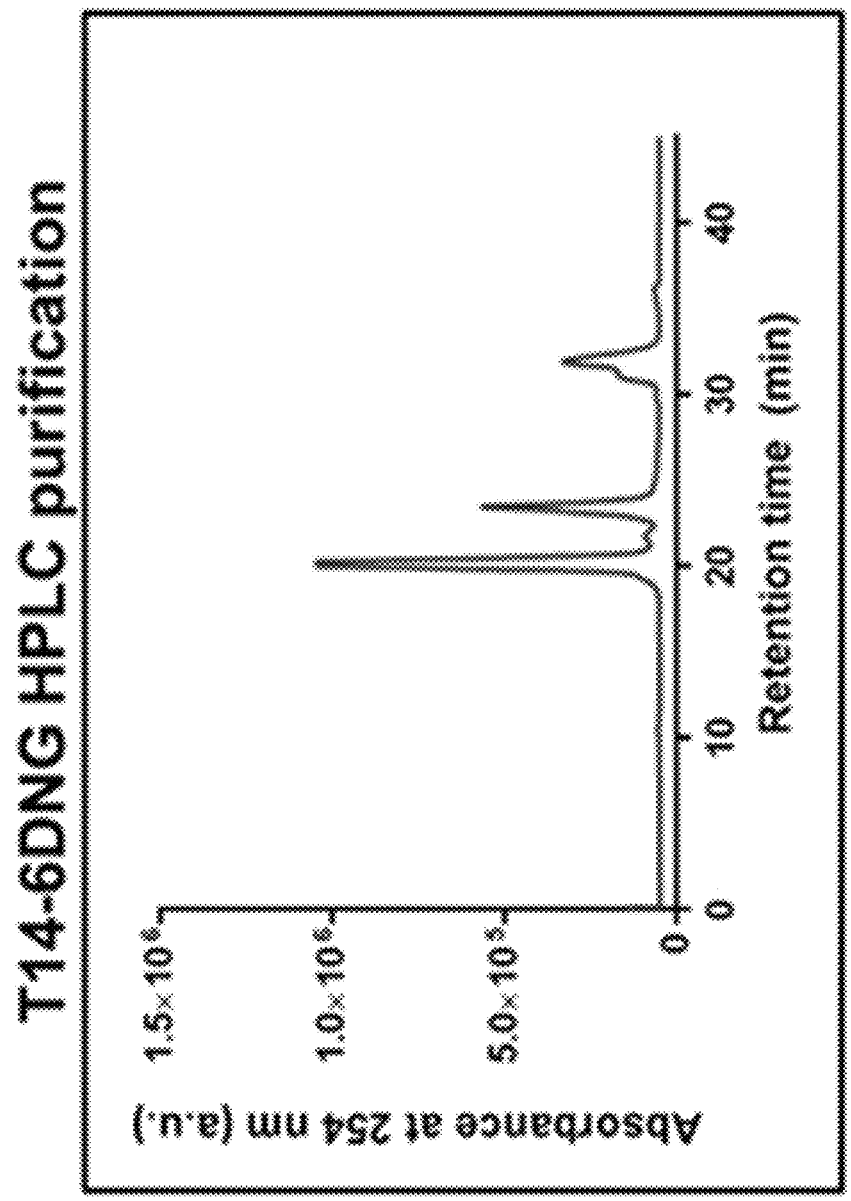
Figure 23C:
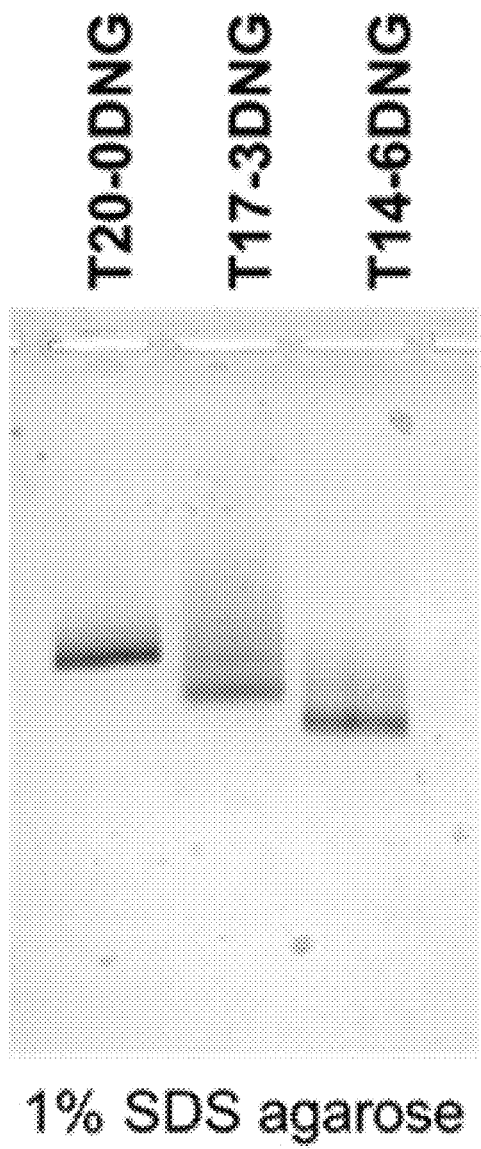
Figures 23D, 23E:
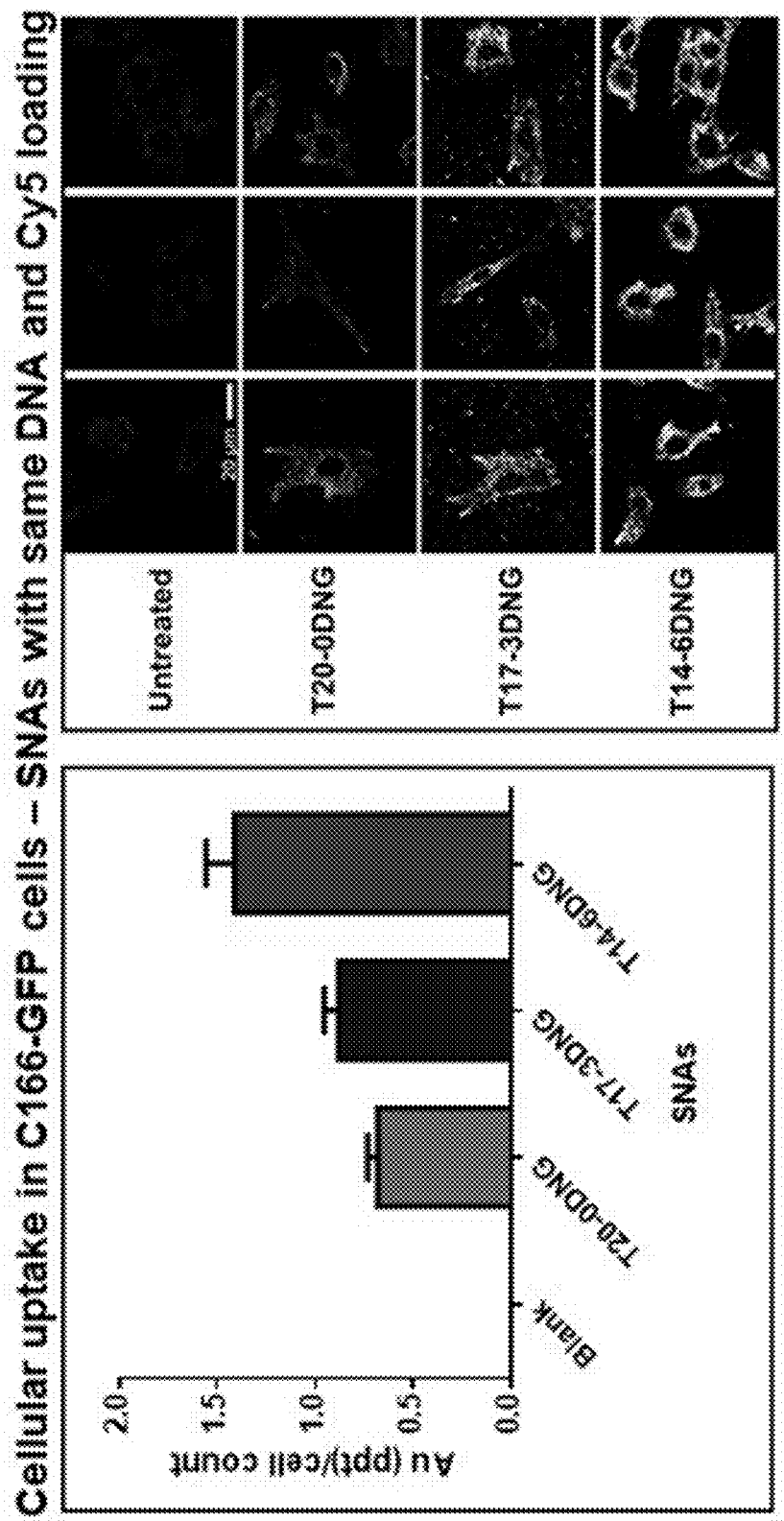

FIG. 22 shows confocal microscopy images of cells incubated at 3 nM by gold in Opti-MEM™ reduced serum media at 4° C. for 2 hours. Plates were rinsed with PBS and fixed with 2% paraformaldehyde. The images indicate that increasing the number of surface DNG modifications on SNAs leads to increased cellular uptake. Green: GFP, Red: Cy5-labeled SNAs.

Example 10

Cellular Uptake of SNAs after Fucoidan Treatment

The effect of position and number of DNG inserts on cellular uptake of SNAs was observed in cells treated with fucoidan. This experiment probed whether DNG-modified SNAs can enter cells through additional pathways than non-modified SNAs.

C166-GFP cells in Dulbecco's Modified Eagle Medium with fetal bovine serum (DMEM+FBS) at 37° C. pre-treated with PBS or fucoidan (50 µg/mL in PBS) for 30 minutes. SNAs (0, 1, 2, or 3 DNG at 5' end) were then added at 10 nM by gold for 30 minutes at 37° C. Cells were triple-rinsed with PBS containing heparin at 37° C. for 5 minutes each after each incubation, trypsinized, and fixed with 4% paraformaldehyde for analysis by flow cytometry. Measurements were made in triplicate.

Figure 24:
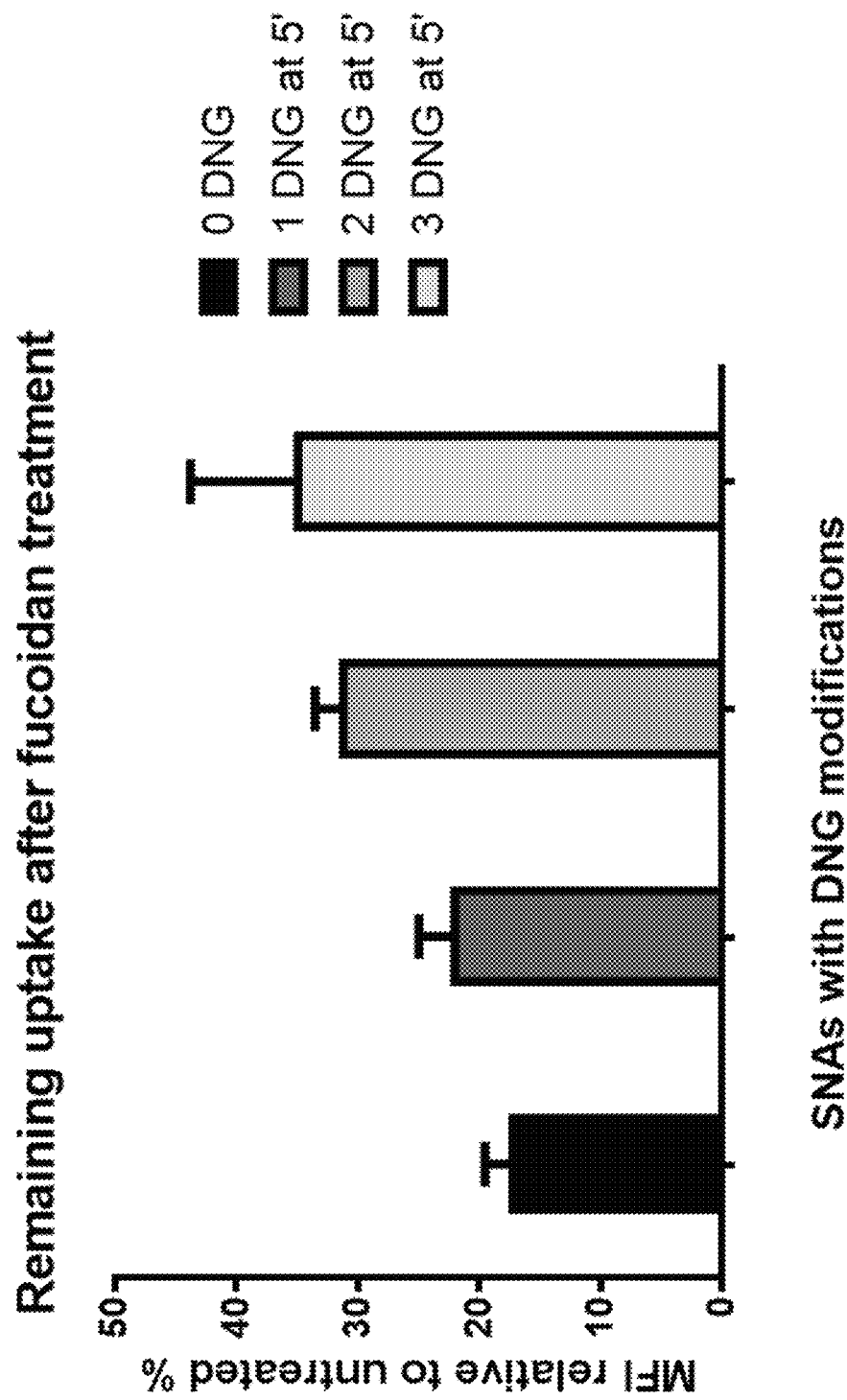
FIG. 24 is a chart showing that SNAs with increasing numbers of DNG modifications are increasingly less dependent on scavenger A receptors for cellular uptake, contrary to unmodified SNAs.

It was observed that SNAs with increasing numbers of DNG modifications are increasingly less dependent on scavenger A receptors for cellular uptake, contrary to unmodified SNAs (FIG. 24). Fucoidan blocks the biological pathway that most SNAs use to enter cells. It was observed that DNG modified SNAs can still enter cells despite fucoidan treatment, and more DNG modifications increase the SNA's ability to enter cells when treated with fucoidan. This suggests that DNG-modified SNAs can follow an uptake pathway different from traditional SNAs that is not sensitive to fucoidan.

Example 11

Cellular Uptake of SNAs after Cholesterol Depletion

The effect of position and number of DNG inserts on cellular uptake of SNAs was observed in cells treated with methyl-β-cyclodextrin (MβCD) in order to acutely deplete them of cholesterol.

C166-GFP cells in Dulbecco's Modified Eagle Medium with fetal bovine serum (DMEM+FBS) at 37° C. pre-treated with PBS or inhibitor (MβCD, 50 µg/mL in PBS) for 30 minutes. SNAs (0, 1, 2, or 3 DNG at 5' end) were then added at 10 nM by gold for 60 minutes at 37° C. Cells were triple-rinsed with PBS containing heparin at 37° C. for 5 minutes each after each incubation, trypsinized, and fixed with 4% paraformaldehyde for analysis by flow cytometry. Measurements were made in triplicate.

Figure 25:
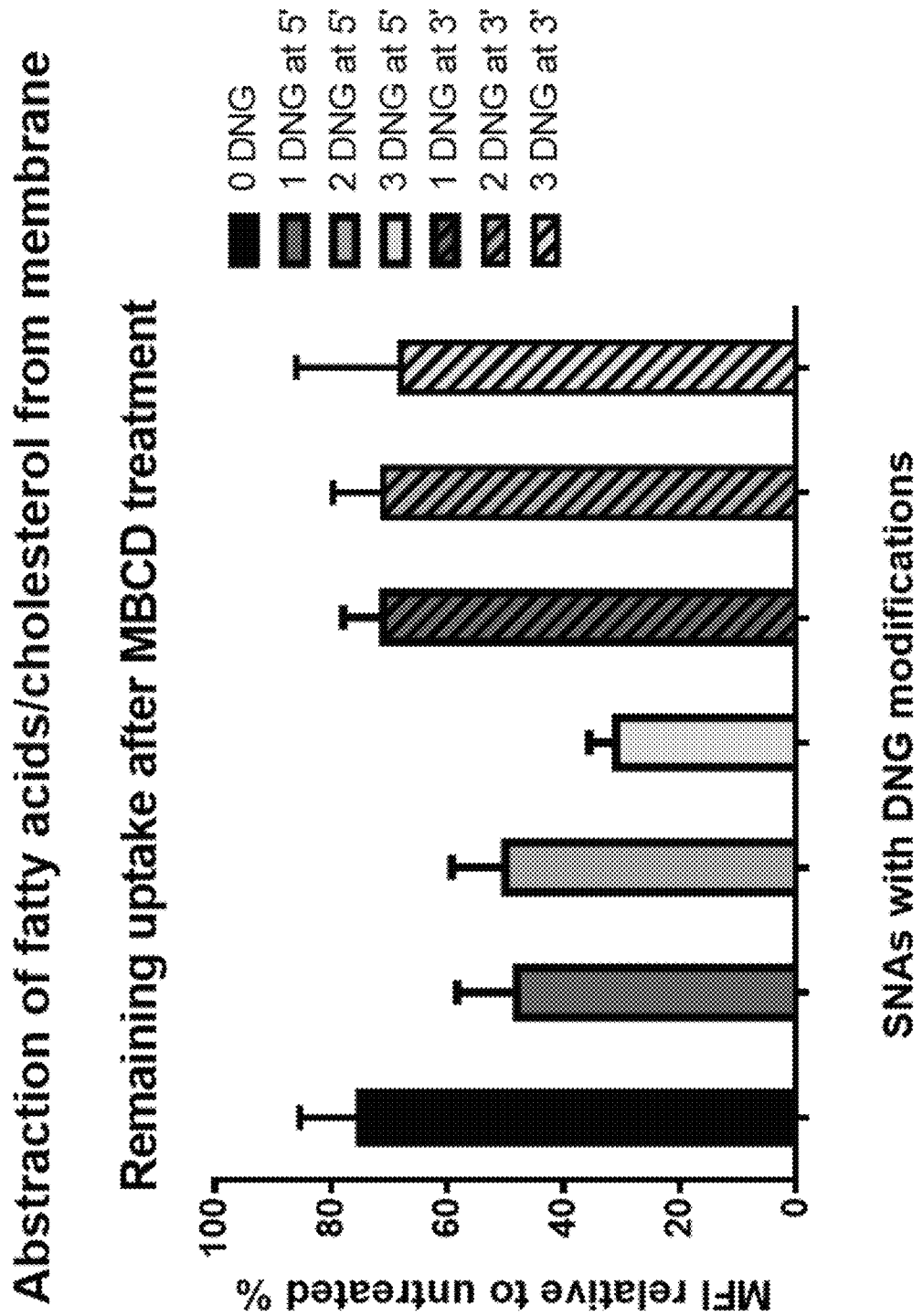
FIG. 25 is a chart showing the uptake of SNAs with DNG modifications at the 5' end of oligonucleotides decreases in C166-GFP cells treated with methyl-β-cyclodextrin (MβCD) as the number of DNG modifications increases.
Figure 26:
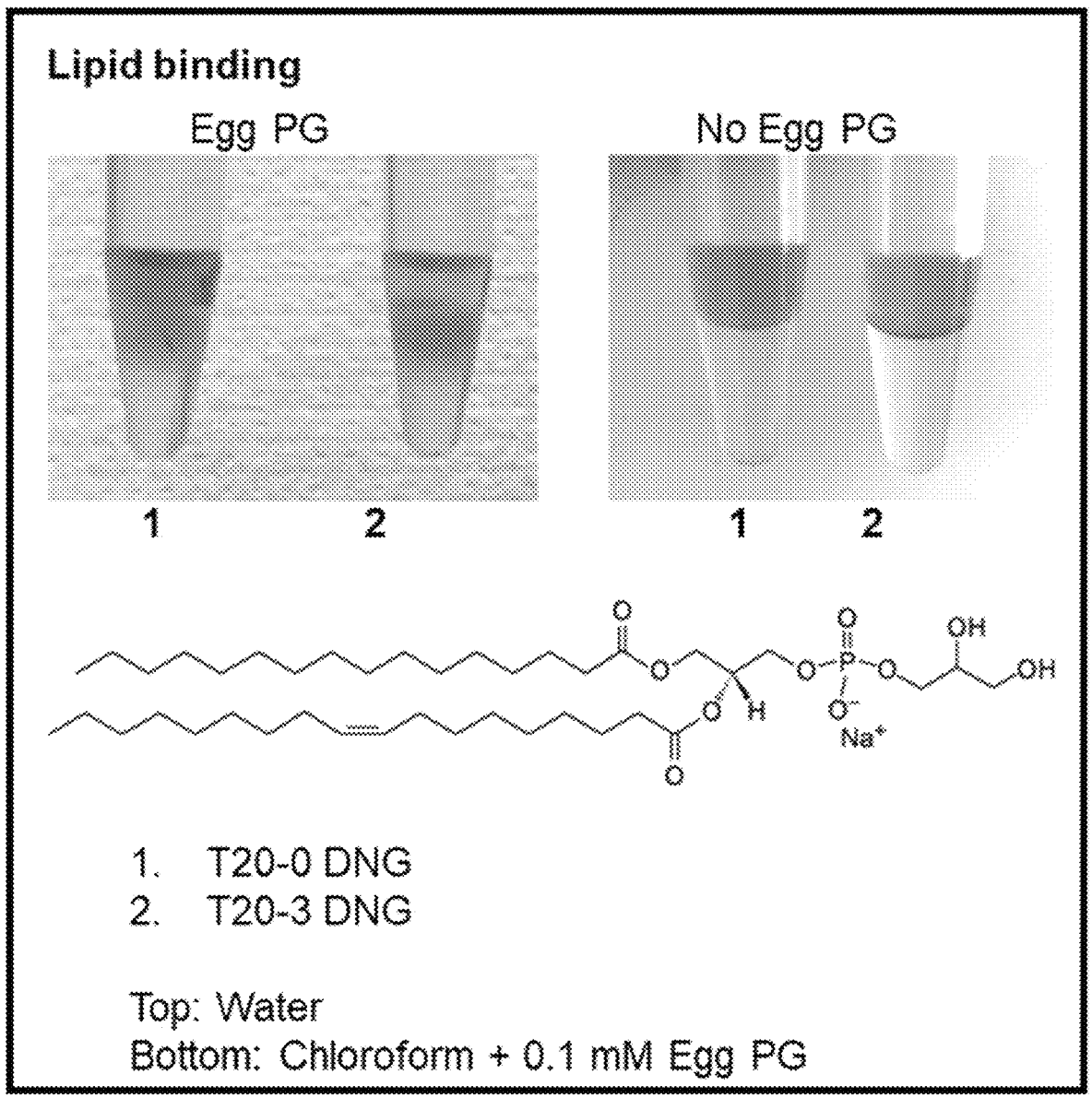
FIG. 26 shows that SNAs with DNG modification partition at the interface between layers/emulsions of water and chloroform containing egg phosphatidylglycerol (egg PG).
Figure 27A:
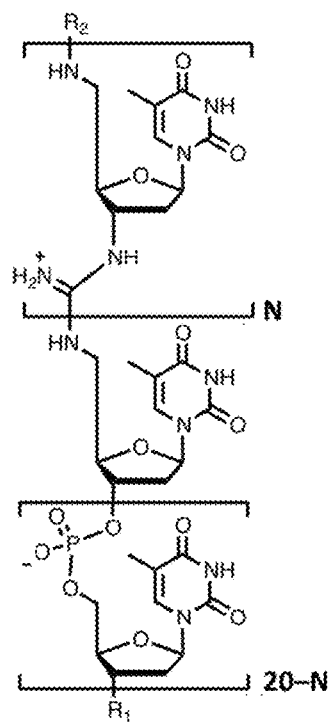
FIGS. 27A-27D show that DNA-DNG chimeras can be purified by HPLC if the number of DNG linkages represents 30% of the oligonucleotide or less.
Figure 27B:
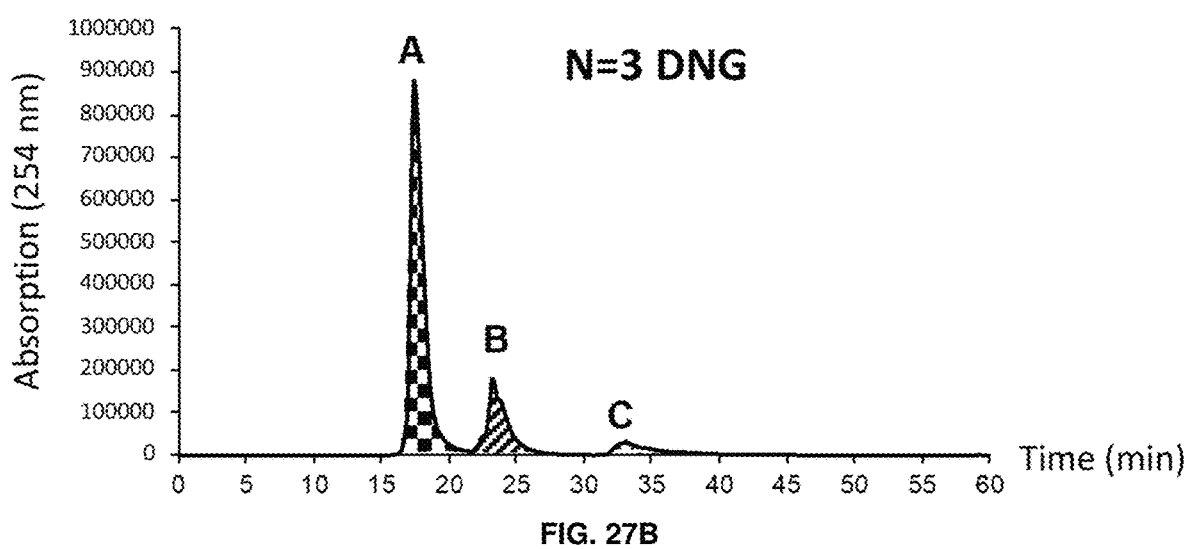
Figure 27C:
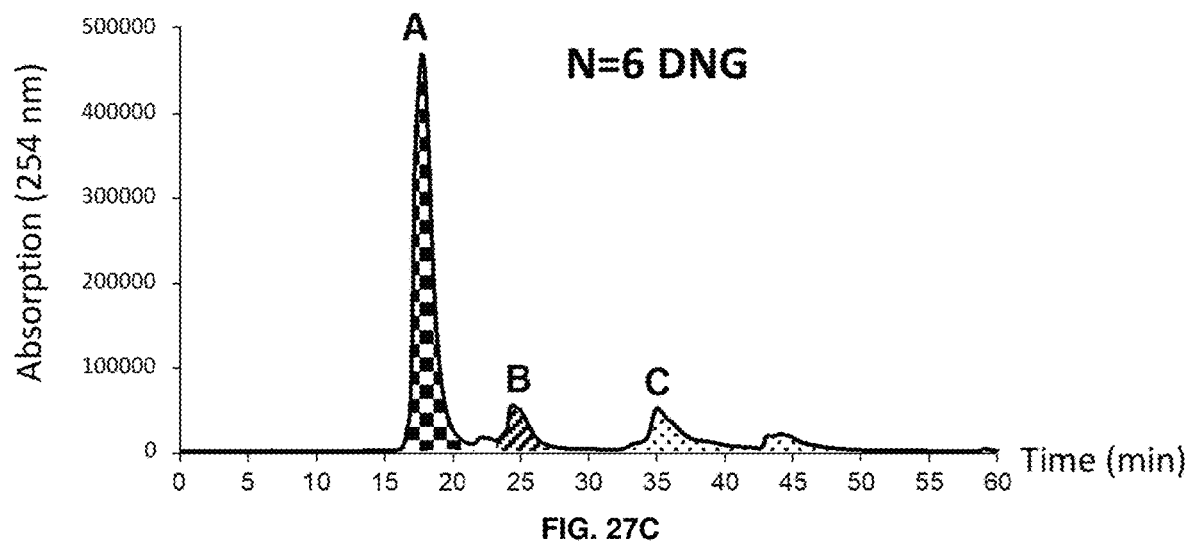
Figure 27D:
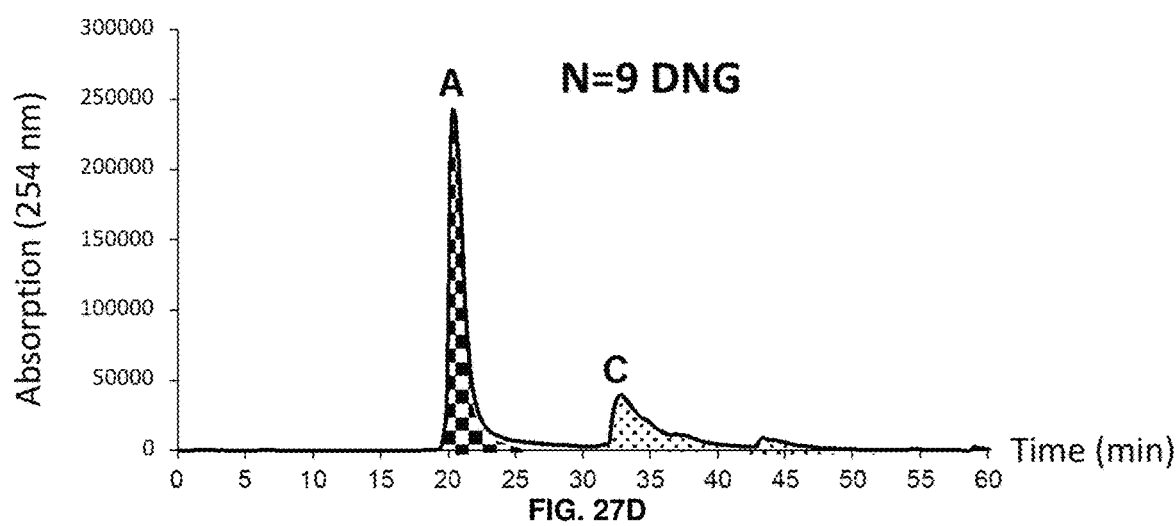
Figure 28A:
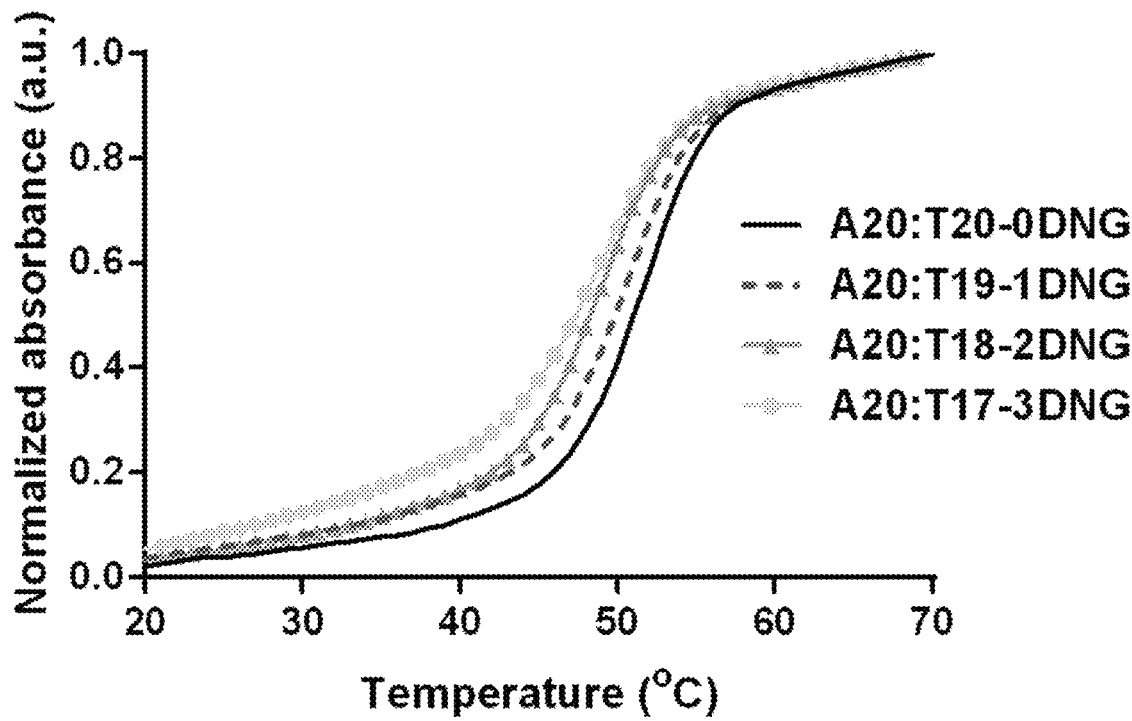
FIGS. 28A-28D show that DNG modifications in DNA-DNG chimeras destabilize duplex formation and reduce the melting cooperativity.
Figure 28B:
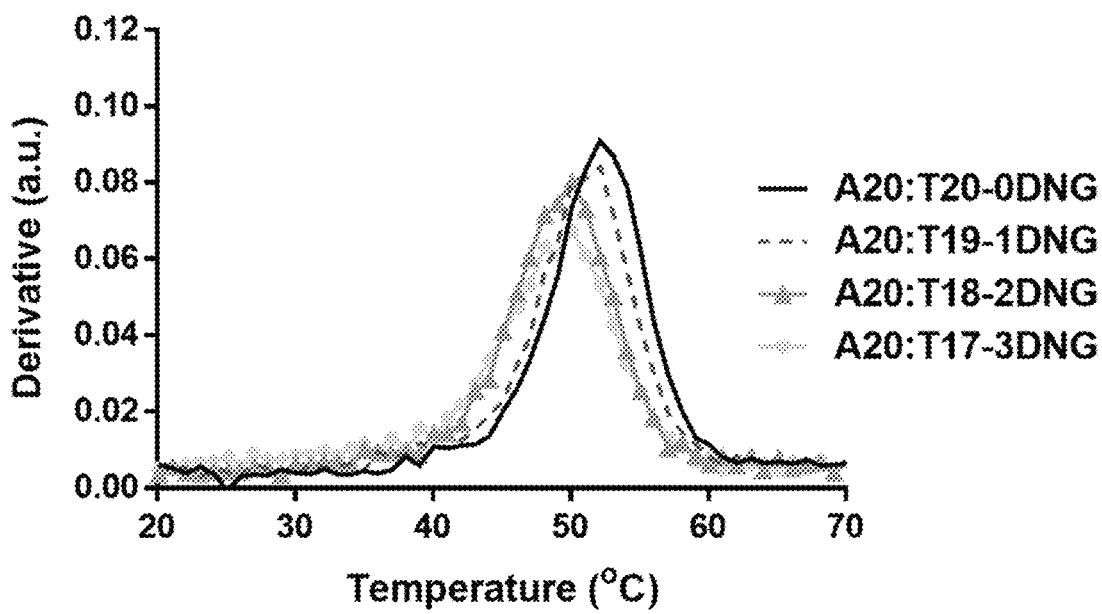
Figure 28C:
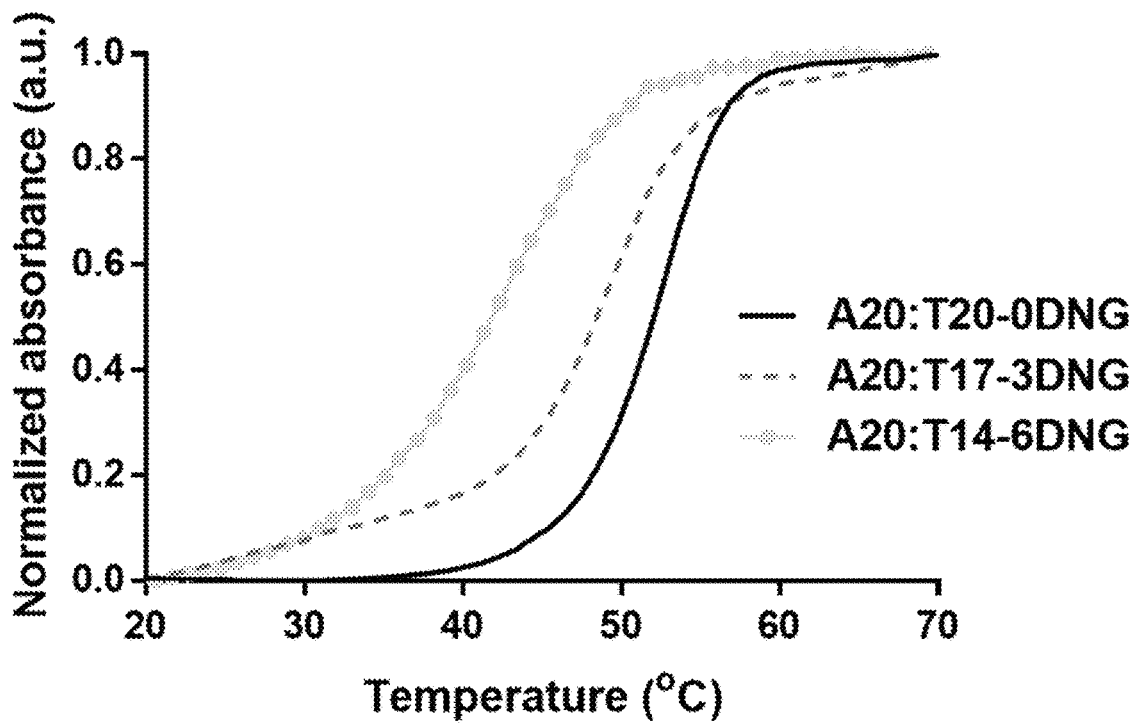
Figure 28D:
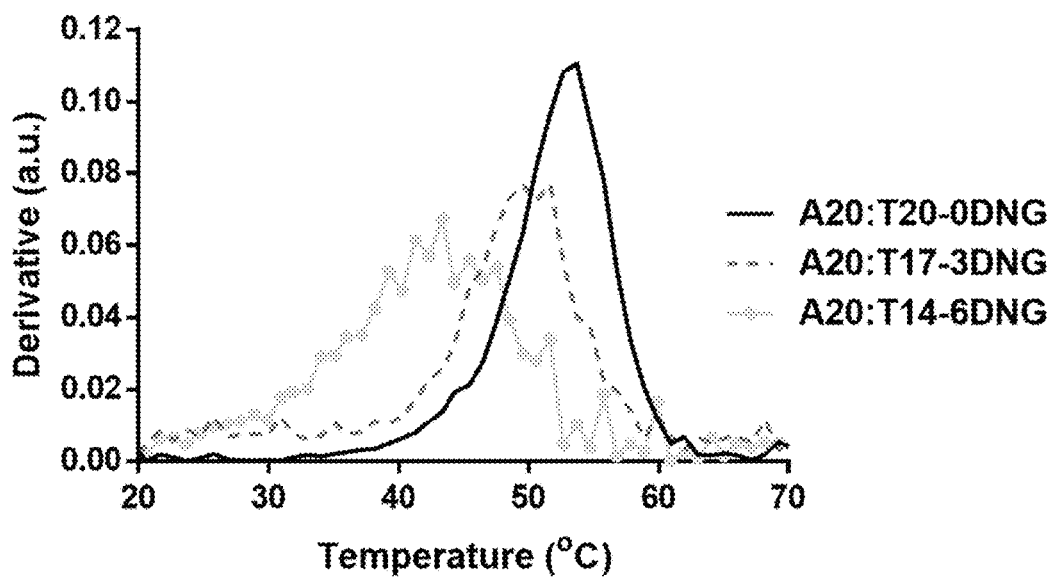
Figure 29A:
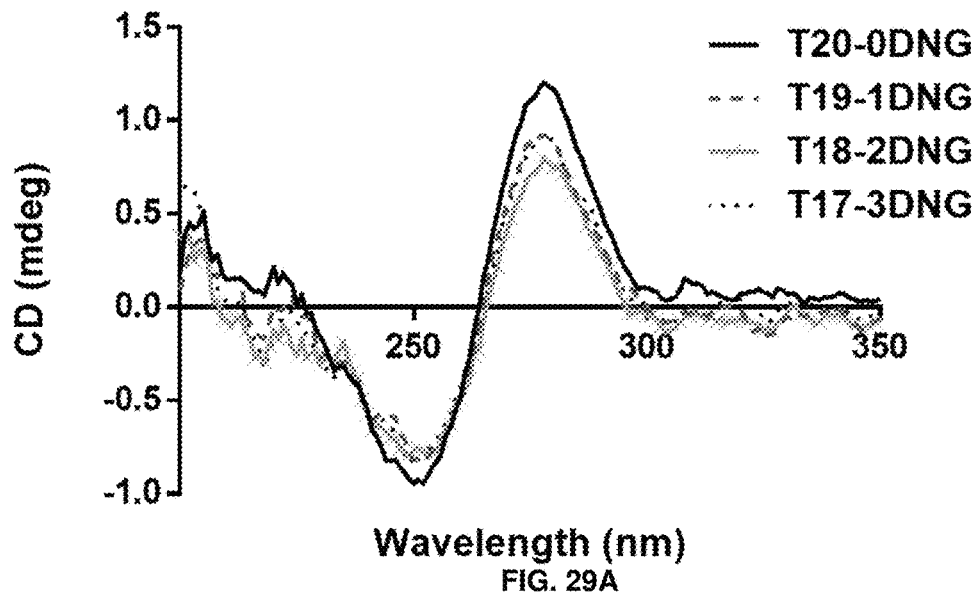
FIGS. 29A-29C show that DNG modifications in DNA-DNG chimeras reduce circular dichroism signal compared to DNA oligonucleotides of the same length.
Figure 29B:
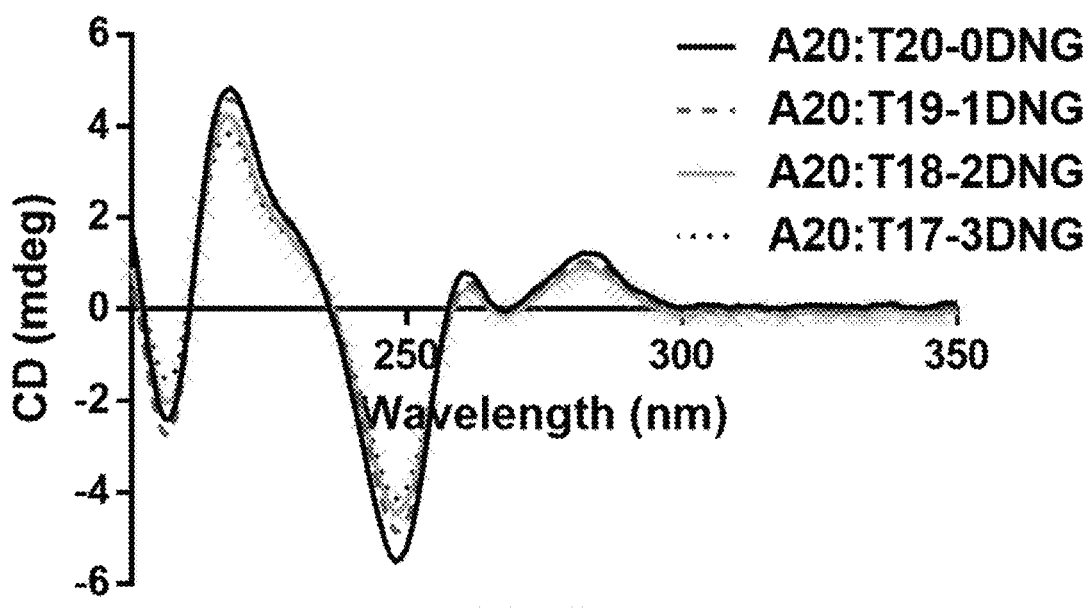
Figure 29C:
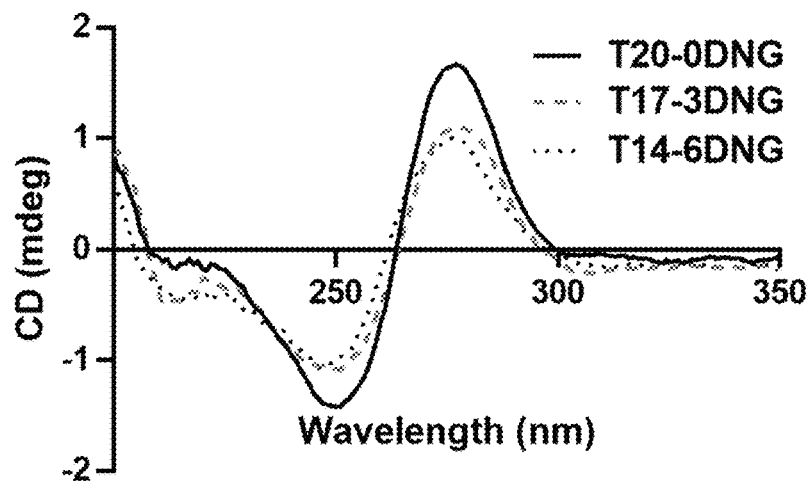
Figure 30A:
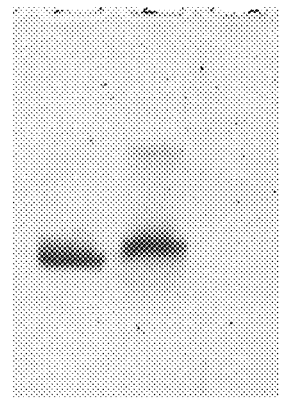
FIGS. 30A and 30B show DNA-DNG chimeras with increasing numbers of DNG inserts at the 5' end show reduced mobility on gel, consistent with an increase in cationic character and less propensity to stain using standard DNA dyes.
Figure 30B:
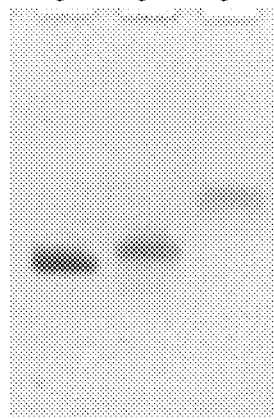
Figure 31A:
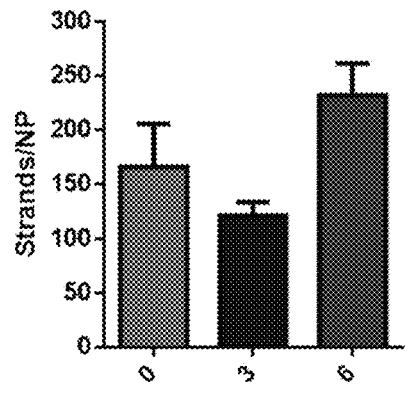
FIGS. 31A-31C show SNAs with increasing number of DNG inserts near their surface can be synthesized using either the salt aging approach or the freezing-thawing method. DNG SNAs made using the salt aging approach show monodisperse populations as opposed the DNG SNAs made using the freeze-thawing method, which tend to aggregate more.
Figure 31B:
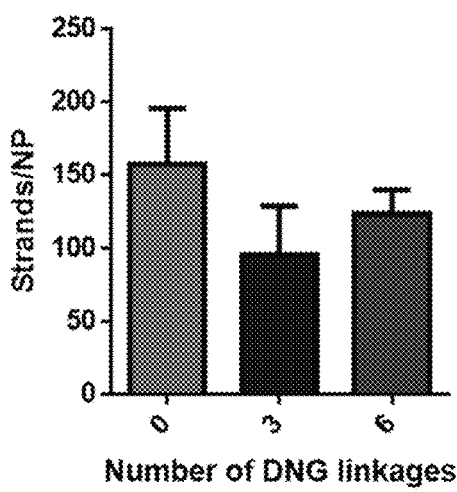
Figure 31C:
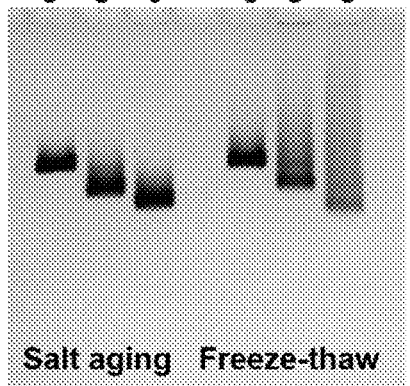
Figure 32A:
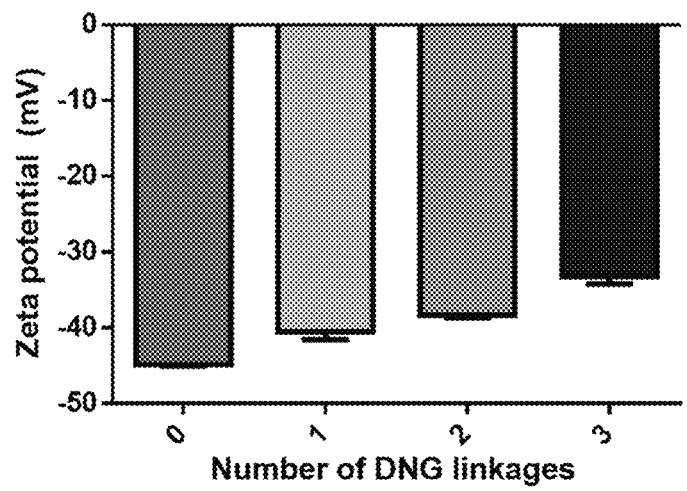
FIGS. 32A and 32B shows that increasing the number of DNG inserts near the surface of SNAs drastically reduces their surface charge.
Figure 32B:
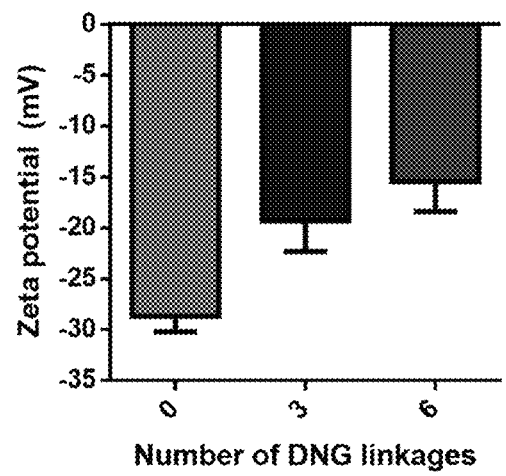
Figure 33:
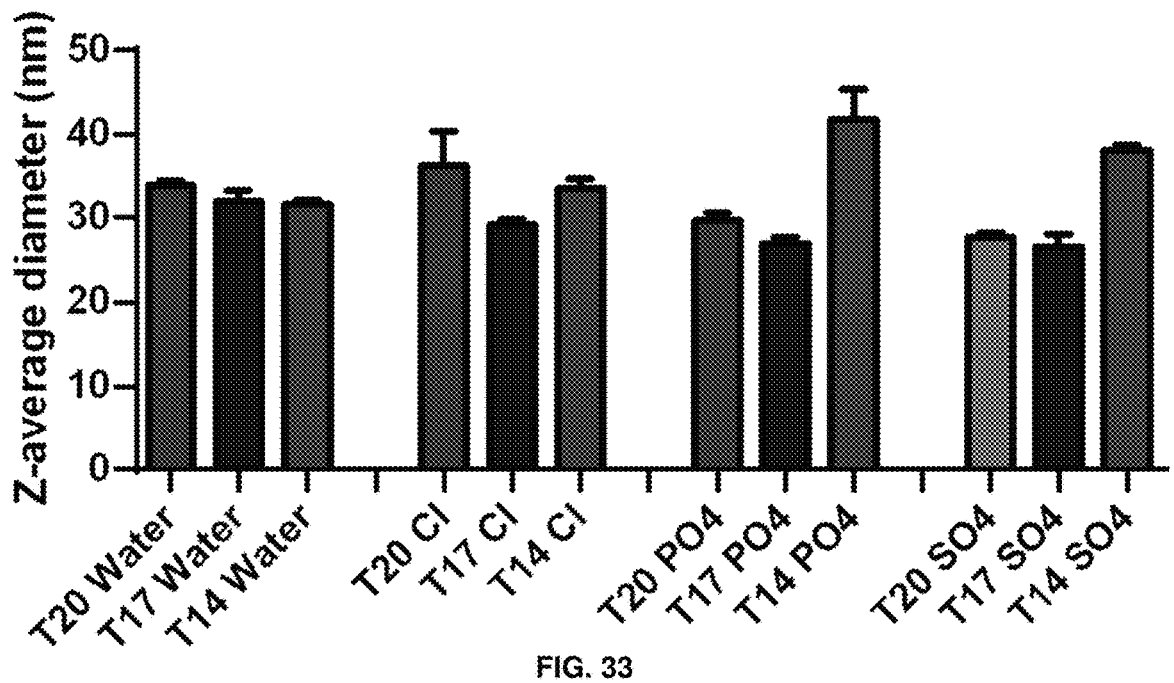
FIG. 33 shows that the apparent size (hydrodynamic diameter) of DNG SNAs relative to unmodified SNAs is influenced by the nature of counterions present in solution.
Figure 34A:
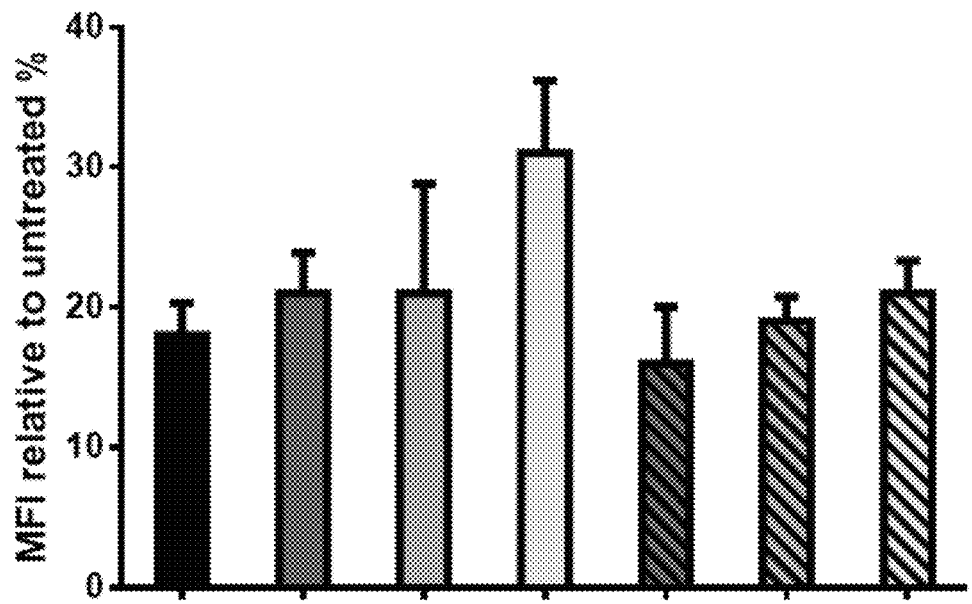
FIGS. 34A-34D show that DNG SNAs can elicit new cell entry mechanisms when compared to unmodified SNAs.
Figure 34B:
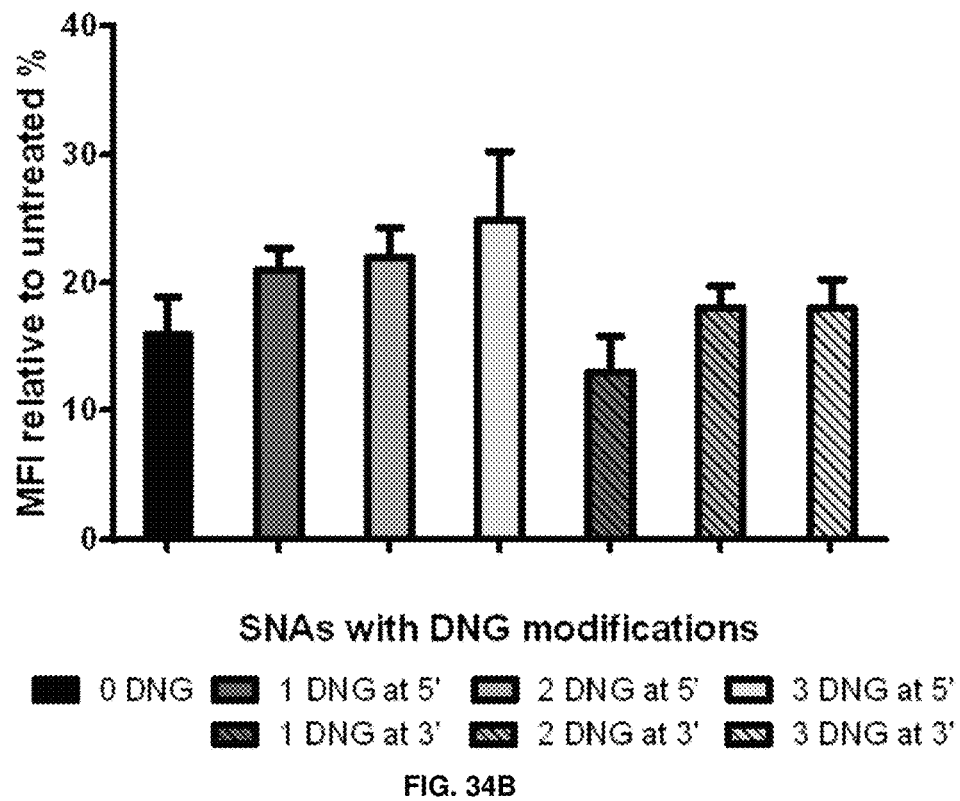
Figure 34C:
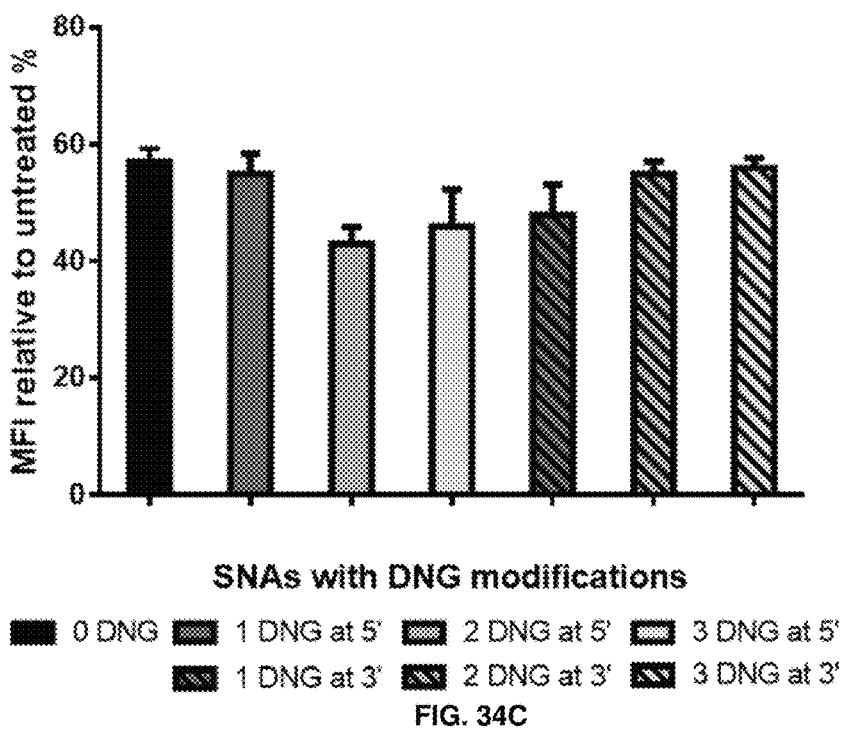
Figure 34D:
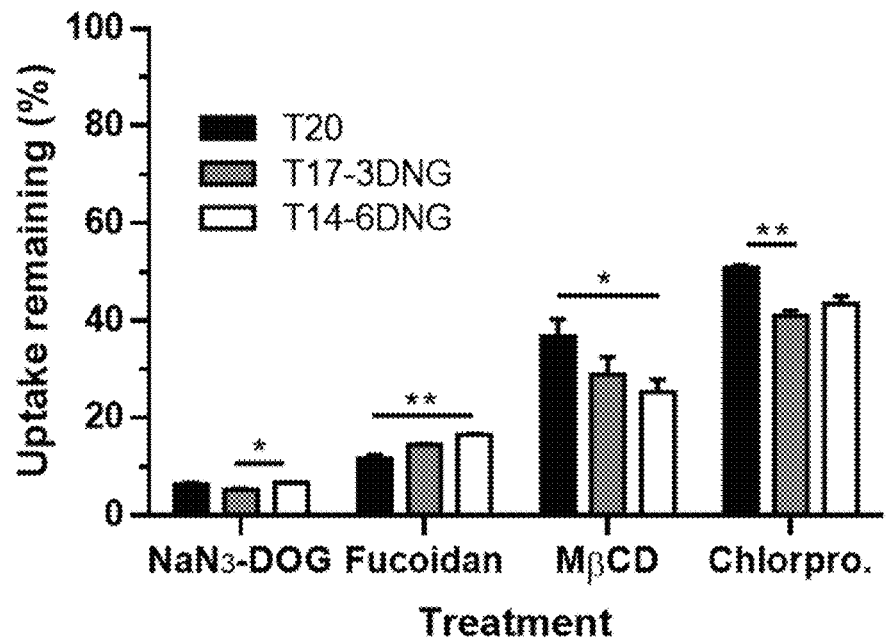

It was observed that SNAs with DNG modifications rely on fatty acids and cholesterol for cellular uptake, contrary to unmodified SNAs. This effect scales with the number of DNG inserts (see FIG. 25). Partitioning of SNAs was observed at the interface between water/chloroform and egg phosphatidylglycerol layers and emulsions (see FIG. 26). Without being bound by theory, this is thought to result from binding of DNG-modified SNAs to lipids.

Various aspects of the disclosure are further described and depicted on the following pages.

What is claimed:

1. A spherical nucleic acid (SNA) comprising a nanoparticle functionalized with an oligonucleotide comprising at least one deoxynucleic guanidine modification (DNG) located at an outer surface of the SNA, and wherein the SNA exhibits increased cellular uptake compared to an unmodified SNA.

2. The SNA of claim 1, wherein the nanoparticle comprises an inorganic material.

3. The SNA of claim 1, wherein the nanoparticle comprises gold, silver, or platinum.

4. The SNA of claim 1, wherein the nanoparticle comprises an organic material.

5. The SNA of claim 4, wherein the nanoparticle comprises a liposome.

6. The SNA of claim 1, wherein the oligonucleotide comprises 1 to 20 nucleotides.

7. The SNA of claim 1, wherein the oligonucleotide comprises 1 to 10 DNGs.

8. The SNA of claim 1, wherein at least one DNG comprises thymine.

9. The SNA of claim 1, wherein the oligonucleotide comprises at least one DNG at the 3' end, or at both the 5' and 3' ends.

10. A method for transfecting a cell comprising contacting the cell with the SNA of claim 1.

11. A spherical nucleic acid (SNA) comprising a nanoparticle functionalized with an oligonucleotide comprising at least one deoxynucleic guanidine (DNG) modification (DNG), wherein the oligonucleotide has a ratio of DNG to phosphate linkages of from 1:1 to 1:6.

12. The SNA of claim 1, wherein the oligonucleotide comprises at least one DNG at the 5' end.

13. The SNA of claim 1, wherein the oligonucleotide comprises 12 to 18 nucleotides.

14. The SNA of claim 1, wherein the oligonucleotide has a ratio of DNG to phosphate linkages is from 1:1 to 1:6.

15. The SNA of claim 11, wherein the oligonucleotide comprises 12 to 18 nucleotides.

* * * * *